United States Patent [19]

Sanford et al.

[11] Patent Number: 5,204,253

[45] Date of Patent: Apr. 20, 1993

[54] METHOD AND APPARATUS FOR INTRODUCING BIOLOGICAL SUBSTANCES INTO LIVING CELLS

[75] Inventors: John C. Sanford; Michael J. DeVit, both of Geneva, N.Y.; Ronald F. Bruner, Sewell, N.J.; Stephen A. Johnston, Durham, N.C.

[73] Assignee: E. I. Du Pont de Nemours and Company, Wilmington, Del.

[21] Appl. No.: 529,989

[22] Filed: May 29, 1990

[51] Int. Cl.$^5$ ...................... C12N 15/00; C12N 15/89; C12M 1/00

[52] U.S. Cl. ............................... 435/172.3; 435/172.1; 435/287; 435/52; 435/53; 435/85

[58] Field of Search .......................... 435/172.1-172.3, 435/240.2, 240.1, 284, 287; 935/52, 53, 85; 604/68-70; 124/61, 71, 73

[56] References Cited

U.S. PATENT DOCUMENTS 4,945,050 7/1990 Sanford et al. .................... 435/172.1
5,015,580 5/1991 Christou et al. .................. 435/172.3

FOREIGN PATENT DOCUMENTS 0270356 6/1988 European Pat. Off. .
0331855 9/1989 European Pat. Off. ............ 435/284

OTHER PUBLICATIONS

Proceedings of the National Academy of Sciences, vol. 88, No. 7, Apr. 1991, pp. 2726-2730.
Journal of Particulate Science and Technology, vol. 5, No. 1, 1987, pp. 27-37.
Trends in Biotechnology, vol. 6, No. 12, Dec. 1987, pp. 299-302.
Sanford, et al., J. Part. Sci. and Tech., vol. 5, pp. 27-37 (1987).
Sanford, Trends in Biotechnology, vol. 6, pp. 299-302 (1988).
Klein, et al., Nature, vol. 327, pp. 70-73 (1987).
Klein, et al., Proc. Natl. Acad. Sci., vol. 85, pp. 4305-4309 (1988).
Klein, et al., Biotechnology, vol. 6, pp. 559-563 (1988).
Johnston, et al., Science, vol. 240, pp. 1538-1544 (1988).
Armeleo, Current Genetics, vol. 17, pp. 97-103 (1990).
Fox, et al., PNAS, vol. 85, pp. 7288-7292 (1988).
Blowers, et al., The Plant Cell, vol. 1, pp. 123-132 (1989).
Daniell, et al., PNAS, vol. 87, pp. 88-92 (1990).
Zelenin, et al., FEBS Letters, vol. 244, pp. 65-67 (1989).
Morikawa, et al., Appl. Microbiol. Biotechnol., vol. 31, pp. 320-322 (1989).
Oard, et al., Plant Physiology, vol. 92, pp. 334-339 (1989).
Moynahan et al., "Development of Jet Injection ... ", Brit. Med. Journ. (1965), pp. 1541-1543.
LaChapelle et al., "Tatagges Permanents ... ", Ann. Dermatol. Venereol. vol. 109 (1982) pp. 939-946.
Sanford, "Biolistic Plant Transformation", Physiologia Plantarium, vol. 79 (1990), pp., 206-209.

*Primary Examiner*—Robert J. Warden
*Assistant Examiner*—William H. Beisner

[57] ABSTRACT

A process is described which uses a "cold" gas shock to accelerate microprojectiles wherein particles are presented to the gas shock on a planar surface perpendicular to the plane of expansion of the gas shock wave. Several different apparatus capable of accomplishing this method are described.

35 Claims, 9 Drawing Sheets

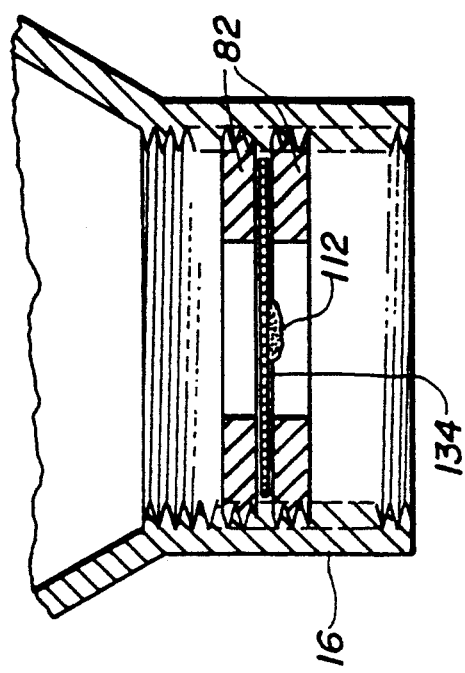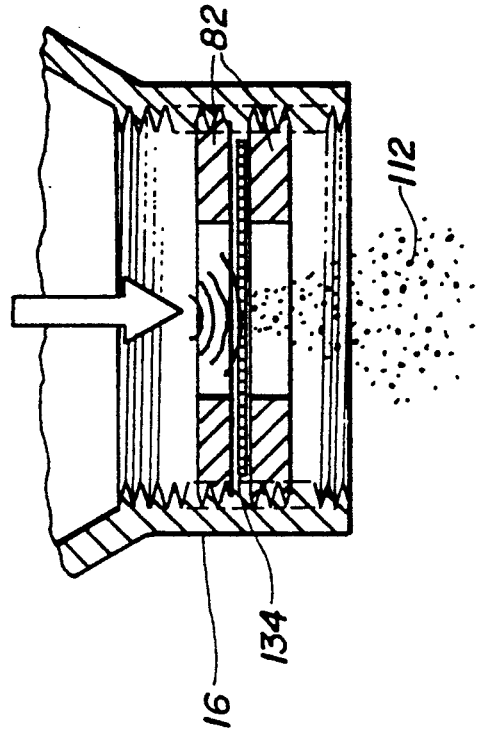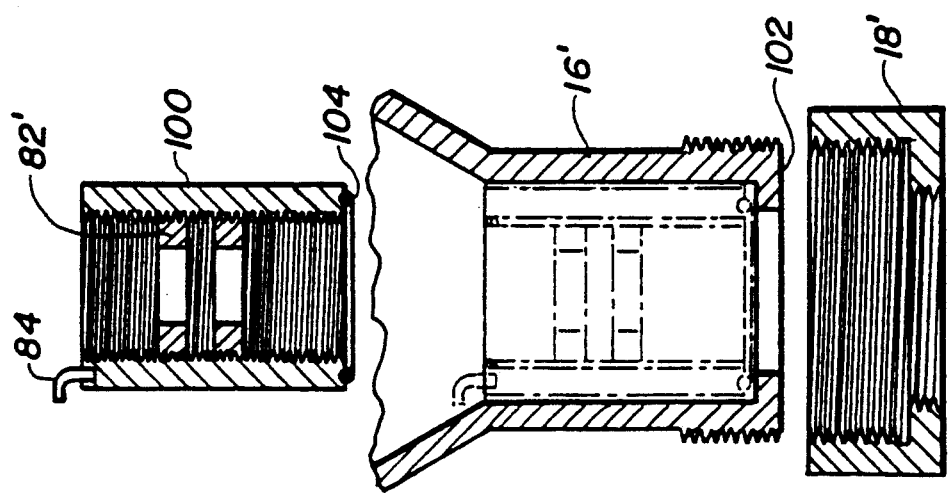

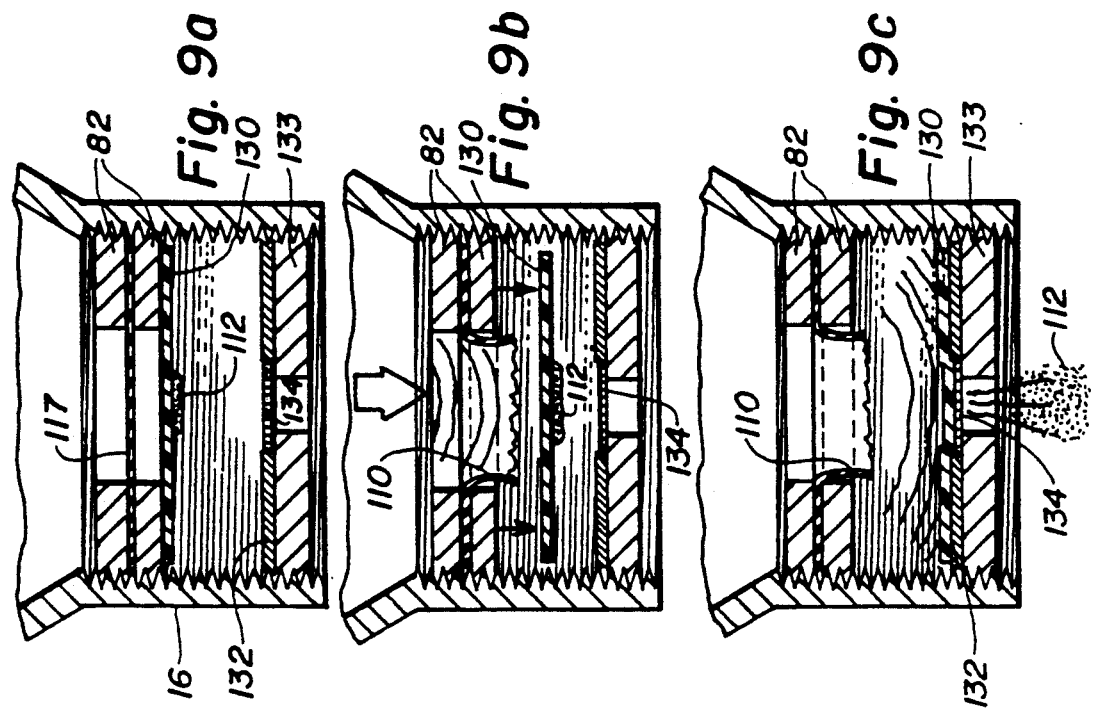
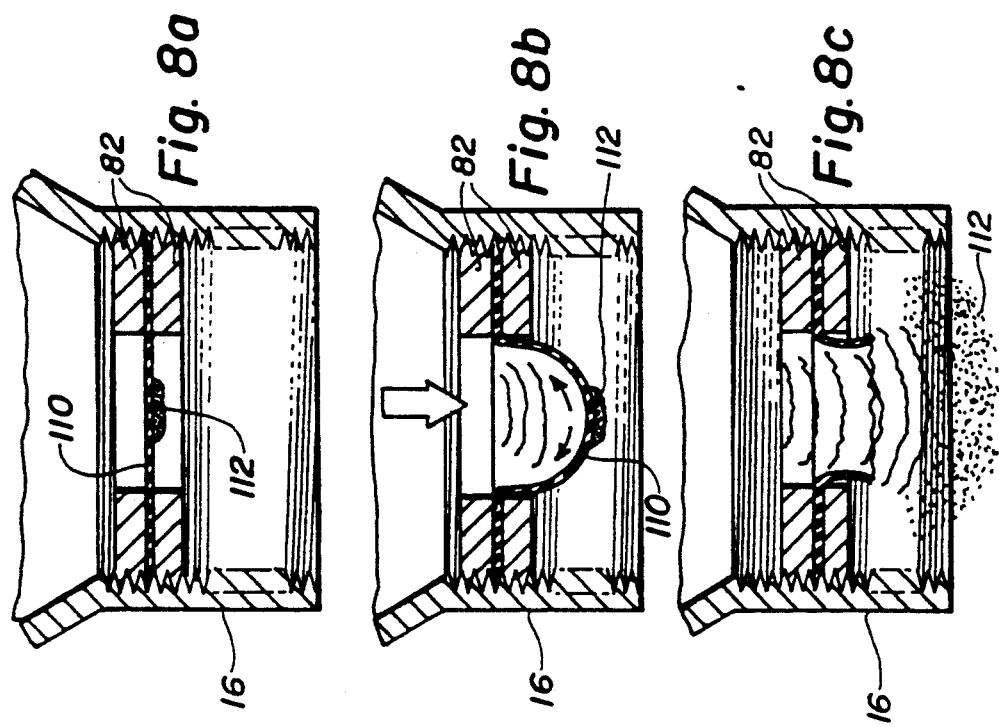

METHOD AND APPARATUS FOR INTRODUCING BIOLOGICAL SUBSTANCES INTO LIVING CELLS

FIELD OF THE INVENTION

This invention relates to an improved method and apparatus for introducing biological substances into living cells and/or tissues.

BACKGROUND OF THE INVENTION

The transformation of living cells by bombardment with biological substances such as heterologous DNA or RNA is described in a patent application entitled Method For Transporting Substances Into Living Cells and Tissues and Apparatus Therefor, by Sanford et al., U.S. Ser. No. 06/670,771, filed Nov. 13, 1984 now U.S. Pat. No. 4,945,050. An improved apparatus for delivering substances into cells and tissue is described in a patent application filed by Sanford et al. entitled "Biolistic Apparatus for Delivering Substances into Cells and Tissues in a Non-Lethal Manner," U.S. Ser. No. 07/161,807 filed Feb. 29, 1988, also by Sanford et al. The process described involves accelerating particles of an appropriate size to high velocities sufficient to penetrate cell walls and/or cell membranes thereby entering into the cell's cytoplasm, nucleus, or organelles. If the particles are carrying biological substances and the velocity is sufficient to penetrate the cell wall without destroying the cell, the biological substances are introduced into the cell.

In this process, holes formed in the cell membrane need not be any larger than would be achieved using microinjection procedures and need only remain open for a fraction of a second. Biological substances such as RNA and DNA may be carried into the cells by a variety of mechanisms such as precipitating the DNA onto the surface of inert particles such as tungsten spheres, latex beads or ferrite crystals as is described by Sanford et al. DNA in a liquid carrier may be used as well or DNA in solid form may constitute the particles themselves. This process is particularly advantageous because large numbers of cells can be bombarded simultaneously and does not require the manipulation of individual cells.

This process is also described by Sanford et al. in *J. Part Sci. and Tech.* 5:27–37 (1987) and is summarized in a recent review by Sanford in *Trends in Biotechnology* 6:229–302 (1988). The biolistic delivery of DNA into onion cells is described by Klein et al. in *Nature* 327:70–73 (1987). The biolistic delivery into corn cells is described by Klein et al. in *Proc. Natl. Acad. Sci.* 85:4305–4309 (1988) and *Biotechnology* 5:559–563 (1988). The transformations of microbes and organelles was first shown by Johnston et al. in *Science* 240:1538–1541 (1988) and Boynton et al. in *Science* 240:1534–1538 (1988) and Armeleo in *Current Genetics* 17:97–103 (1990). Organelle transformation was further elucidated by Fox et al. in *PNAS* 85:7288–7292 (1988), Blowers et al. *The Plant Cell* 1:123–132 (1989) and Daniell et al. *PNAS* (in press) (1989).

The utility of the process for higher plant transformation has been reviewed by Sanford *Physiologia Plantarum* (in press) (1989) and has been further demonstrated in numerous papers. Further the transformation of higher animal cells using this bombardment technique has been demonstrated in vitro in Zelenin et al. *FEBS Letters* 244: 65–67 (1989) Johnston et al. (in preparation) and Williams et al. *Nature* (submitted) (1990) and most recently in vivo in Johnston et al. (in preparation) Zelenin et al. (in preparation).

Based on these early teachings, various apparatus have been constructed to effect the delivery of particles carrying biological substances.

The apparatus described by Sanford et al. is commercially available from E. I. du Pont de Nemours and Company, Wilmington, Del. in the form of a gunpowder driven device in which the hot gasses generated by a gunpowder discharge form a hot gas shock wave which accelerate a macroprojectile carrying many tiny microprojectiles. When the macroprojectile strikes a stopping plate having a hole therein, the microprojectiles continue their travel, striking the target cells. Morikawa et al. *Appl. Microbiol. Biotechnol.* 31:320–322 (1989) have constructed a device based on the teachings of the Sanford et al. that uses pressurized nitrogen to drive the macroprojectile. Agracetus in European patent application 8731062.4 filed Dec. 2, 1987 (publication number 0270356) describe a macroprojectile accelerator. When the macroprojectile is a thin disk, it is accelerated by the use of a very high voltage discharge, which vaporizes a droplet of water, creating a hot gas which drives the projectile similar to the hot gases generated by the gunpowder discharge.

Dr. Laurie Mets has built a particle accelerator which is based on the same principle described in the Sanford et al. patent application, namely, gas flow entrainment of the particles. Finally Oard et al. (1990) achieved transient gene expression in maize, rice and wheat cells using compressed air to accelerate a cylindrical macroprojectile. *Plant Physiology* 92:334–339 describes the use of such an airgun for propelling DNA coated microprojectiles. A polycarbonate vacuum chamber encloses the airgun muzzle and target material.

While these various apparatus represent various approaches to the problem of how best to accelerate microprojectiles for transferring biological materials into cells and tissues, they all suffer from one or more deficiencies. First of all, many of the apparatus constructed are not flexible as to mode of use. There are a wide array of applications for the ballistic process, each calling for different capabilities, settings, configurations, etc. The existing apparatus tend to be optimal for a single mode of use or for a single application but are not adaptable to plural needs. Secondly, the apparatus available generally does not provide the degree of repeatable results, target-to-target and day-by-day, that is desired. Existing accelerators have a high degree of variability in performance. Also the particle dispersion pattern is poor and not uniform over the target area. Existing apparatus often does not effectively break up particle aggregates and does not allow control over how large an area over which the particles are dispersed.

Most of the existing apparatus is bulky, generally immobile and generally cannot be handheld such as is needed for some veterinary or medical applications. In this connection, most of the apparatus that are available requires that the targets be placed inside a vacuum chamber and are not suited for use on targets larger than such chamber. Whatever the target used, there is a tendency for the accelerator apparatus to damage (or kill) a certain number of the cells, which impairs cell division or cell differentiation. This is especially true when the distance to the target needs to be short, as in medical applications. It is desirable therefor to have better velocity control, less gas blast, less acoustic shock, less high velocity debris, less heat, and less radiant energy.

Apparatus which employs gunpowder or high voltage discharges tend to generate high temperatures. Furthermore, high voltage discharges generate a blinding flash which may generate ultraviolet light and other forms of ionizing radiation. Such may be harmful to the cells being transformed, or the DNA being delivered.

SUMMARY OF THE INVENTION

Many of the deficiencies of the prior art acceleration methods for introducing particles carrying biological materials into a target of cells and/or tissue are overcome utilizing the method of this invention. Such method comprises the steps of accelerating the particles sufficiently to cause them to penetrate the surface of the cells and/or tissues and become incorporated into the interior of the cells and/or tissue without killing the cells and/or tissues and effecting the particle acceleration by subjecting the particles to the force of a gas shock wave generated from an ambient temperature gas (hereinafter referred to as a "cold" gas shock wave). The method for particle acceleration includes positioning the particles on the target side of a planar surface and subjecting the surface to the cold gas shock wave, thereby to accelerate the surface and hence the particles. If the planar surface is a mesh, the particles are optionally entrained into the shock wave. If the sheet is solid and is fixedly secured at its edges, the cold gas shock wave causes distention but not rupture of the membrane thereby launching particles while optionally protecting the target from the shock wave.

Alternatively, if the membrane is fixed and allowed to rupture, the particles are dispersed over a wider region of the target cells. Or, the biological materials may be dispersed on a screen in the path of the gas shock wave. If a restraining screen is positioned between the target cells and a solid, unfixed membrane (a flying disk) flight of the disk will be restrained after a short distance, allowing the particles to be launched and pass through the screen to the target.

Using the various methods set forth above provides a number of alternatives which may be utilized according to the need. For example, the use of a "flying disk" provides protection of the target as well as very high particle speeds. When the particles are simply entrained in the shock wave, the damage to the cells and tissue can be more severe, but velocities may be highest. On the other hand with the use of a distended membrane whose distention is limited by a screen, least cell damage occurs. The rupturable membrane achieves a better dispersion of the particles but tends to increase somewhat the cell damage.

An apparatus for performing the method of this invention includes a closed housing capable of sustaining a vacuum, the housing having a first port for applying a vacuum thereto, a major axis, and a second port lying on the axis, and defining a throat portion opposite the second port encompassing the axis, a high pressure chamber positioned in the second port and adapted to catastrophically release gas stored therein to provide a gas shock wave directed toward the throat portion, and means for positioning the particles in the throat portion for acceleration by the force of a shock wave toward the target. An optional interface, secured to the throat portion, may be provided for coupling the throat portion to the target, when large targets are employed, or where target's exposure to vacuum and/or shock is to be limited. The invention provides flexibility for positioning and launching the particles in the throat portion, each configuration having various advantages and disadvantages.

In short, the apparatus can be seen to have five parts (a) a high pressure gas delivery system; (b) a mechanism to generate an instantaneous gas shock out of the high pressure system; (c) an enclosure into which the gas shock is released, contained and vented; and (d) a throat region which allows for interchangeable inserts which translate the gas shock into microprojectile acceleration, utilizing the force of the gas shock by several diverse mechanisms. Finally, an interchangeable interface mechanism may be used for different types of biological targets ranging from small animals or plants to large animals or plants, to cells contained in a petri dish, etc.

BRIEF DESCRIPTION OF THE DRAWINGS

The invention will be better understood with reference to the attached drawings in which:

FIG. 4 is an alternative construction for the throat portion of the particle accelerator of FIG. 1;

FIGS. 5a and 5b are cross sectional representations of the throat portion of the particle accelerator depicting initial and operated conditions for one embodiment of the particle accelerator constructed to operate in a gas entrainment mode;

FIGS. 8a, 8b and 8c are cross sectional representations of the throat portion of the particle accelerator depicting the initial, intermediate and operated conditions of the particle accelerator when constructed to operate as in a ruptured membrane mode;

FIGS. 9a, 9b and 9c are cross sectional representations of the throat portion of the particle accelerator of this invention constructed to operate as a flying disk and showing the initial, intermediate and operated conditions;

DETAILED DESCRIPTION OF THE PREFERRED EMBODIMENT

Figure 1:
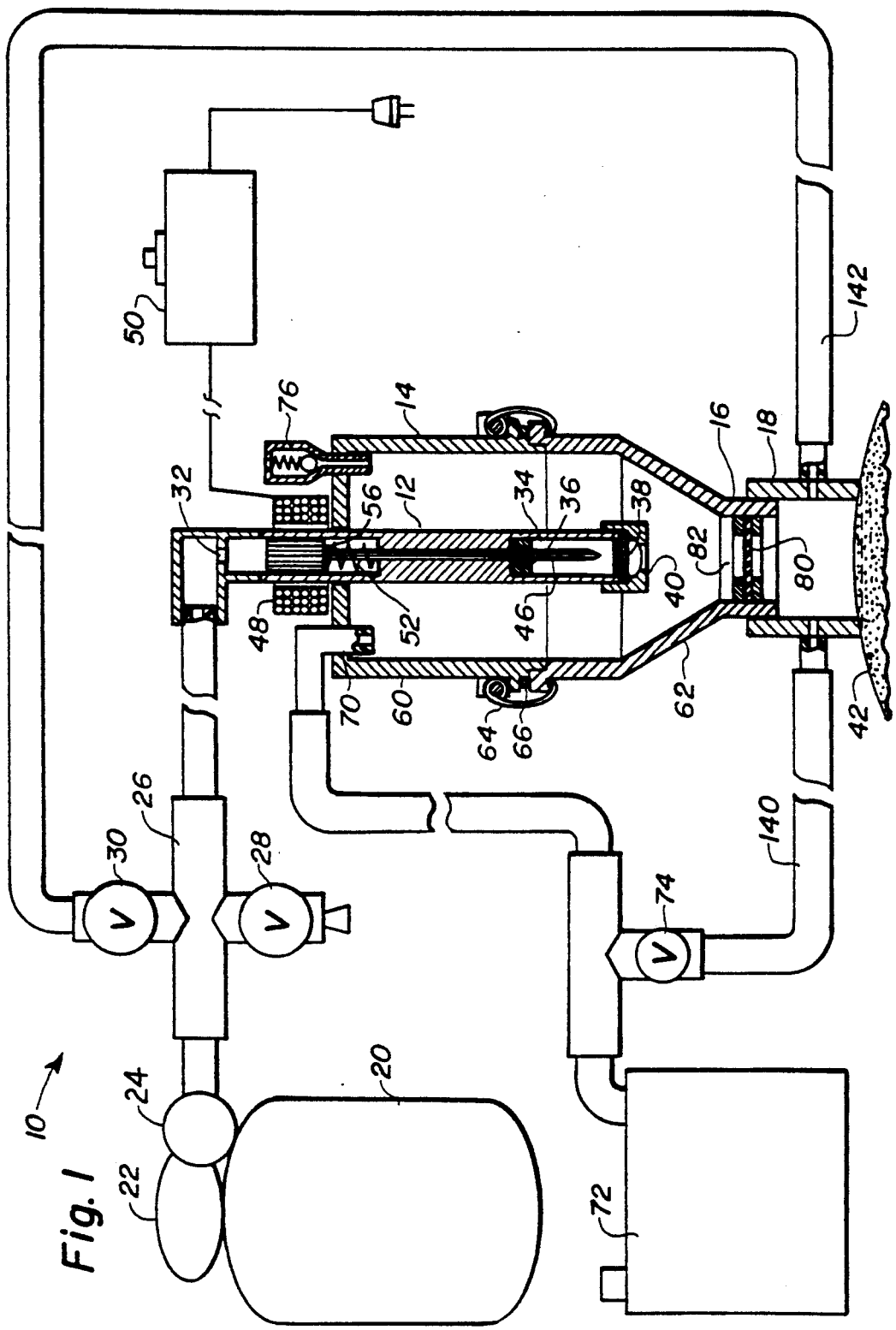
FIG. 1 is a diagrammatic view of a system including an apparatus for introducing particles carrying biological materials into a target of cells and/or tissue constructed in accordance with this invention.
Figure 2:
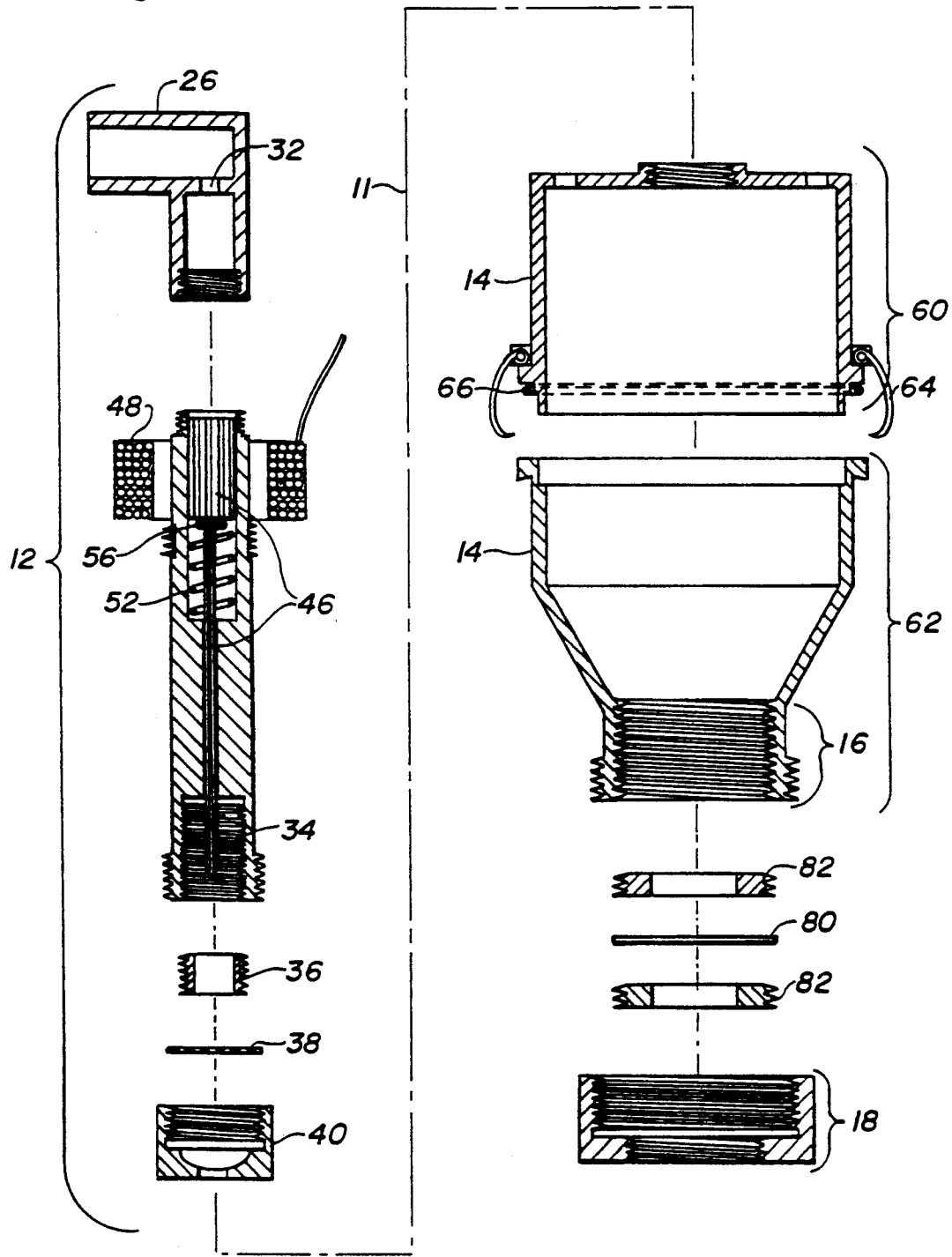
FIG. 2 is a cross section exploded view of the details of the apparatus of FIG. 1.
Figure 3:
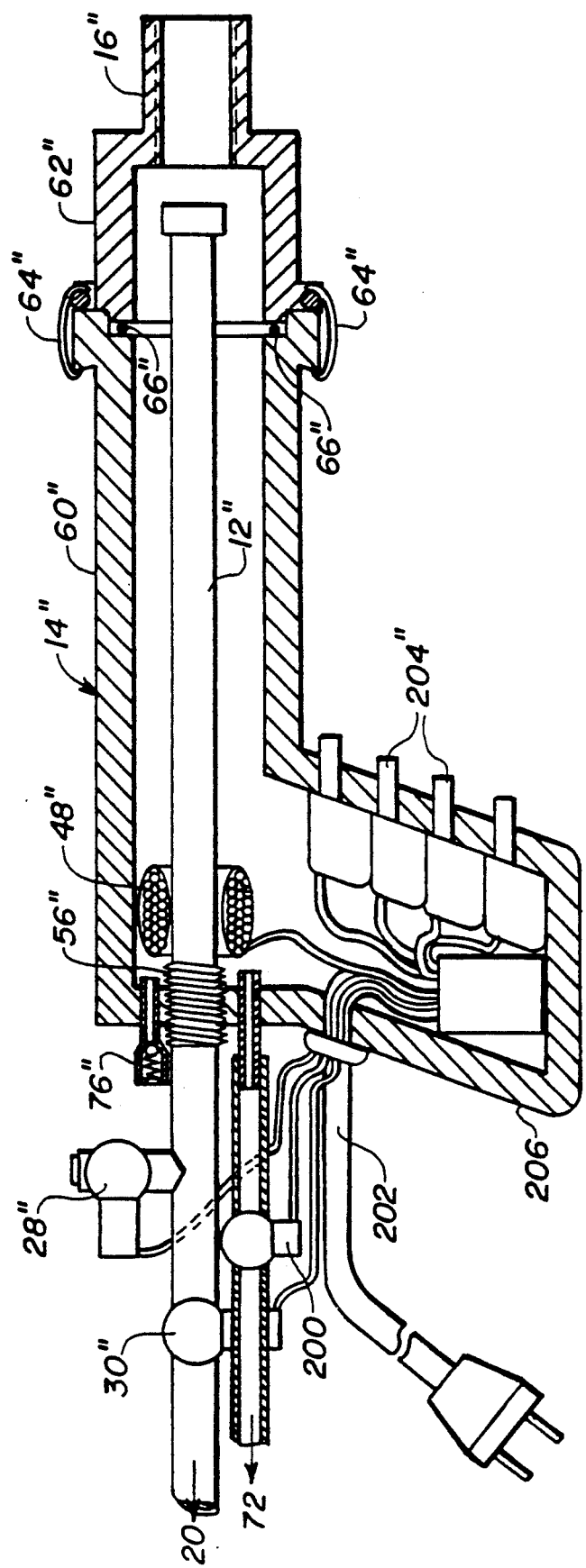
FIG. 3 is an alternative construction of the apparatus of FIG. 1 which is particularly useful as a handheld device.

With reference to FIGS. 1 and 2, the apparatus of the invention may be seen to comprise five parts: (a) a high pressure gas delivery system 10; (b) a shock mechanism 12 to generate an instantaneous gas shock wave out of the high pressure system; (c) an enclosure or housing 14 into which the gas shock wave is released, contained and vented; (d) a throat region 16 of the device, which allows for interchangeable inserts, which translates the gas shock wave into microprojectile acceleration by diverse mechanisms; and (e) an optional interchangeable nozzle or interface mechanism 18 for targeting different types of biological targets.

The high pressure gas delivery system includes a source of gas 20 under high pressure. Typically the gas may be helium because of its light weight and characteristic of having a high speed of expansion. Other preferably inert gases may be used if desired such as nitrogen. Also air, hydrogen, etc. may be used. Gas source 20 is provided with a suitable regulator 22 and pressure indicator 24 and is coupled through suitable tubing 26 to the chamber 12 for generating the instantaneous gas shock wave. A bleed valve 28 and shutoff valve 30 are used. The valve 30 couples the source of gas 20 to the nozzle or interface 18 as will be described.

The shock generating system 12, the details of which are seen more clearly in FIG. 2, receives gas from the tubing 26 through a constriction 32 which serves to limit the flow rate of gas, thereby stabilizing the rupture-activating mechanism and preventing premature firing before the desired pressure is reached. It serves as a gas shock generating system. All of the fittings of the chamber 12, housing 14, throat inserts 18, interface 18, unless otherwise specified, may be made of any suitable material capable of withstanding high pressures or vacuums, such as brass or stainless steel. The constriction 32 also serves to limit the flow of gas through the system after firing in the event that other closure mechanisms fail. Because of the constriction, it takes some seconds to pressurize a high pressure chamber 34 contained in the lower portion of the shock generating system 12.

A valve which can reproducibly be cracked open could replace the constriction, allowing adjustment of the flow rate through the constriction point. The dimensions of the pressurized gas chamber 34 within the shock generating system 12 should be sufficiently large to contain enough gas to allow generation of a powerful gas shock wave but small enough to limit the amount of gas that needs to be vented and which will contribute to the gas impacting onto the biological target. Essentially this chamber area is denoted by the numeral 34. The volume of the chamber 34 may be adjusted by a threaded sleeve insert 36 which may be sized as desired.

The gas shock wave generating mechanism 12 is designed to provide a very sharply defined pressure front which needs to expand freely into an area of relatively low pressure. Release mechanisms suitable for generating the appropriate gas shock wave must open very rapidly. This can be accomplished either by the instantaneous rupture of a membrane, or by the use of a special very fast valve. Due to the lack of availability of truly fast, high pressure valves the embodiment depicted in FIGS. 1 and 2 is preferred which includes a rupturable membrane 38. The membrane is held by an endcap 40 (FIG. 2) threadingly engaged to the cylinder comprising shock generating system 12. The endcap 40 is open at its central portion to allow for the gas to escape downwardly in the direction of a target 42 as will be described. The membrane may be any suitable rupturable material such as Kapton ® polyimide films or Mylar ® polyester films. The characteristics of these type materials will be described below. The use of five 2 mil thick Kapton ® membranes has been used successfully (as an example four-five layers of 2 mil thick Kapton ® membrane will contain 1,200 psi of helium). The cap 40 has a frictional compression seal (not shown). Under this arrangement the pressurized membranes are significantly deformed outwardly but do not rupture spontaneously. Alternatively, a weaker membrane or higher pressures can be used to achieve spontaneous rupture.

In order to assure a sudden rupture of the membrane 38, which must be catastrophic, an active rupture mechanism can be employed in the form of a rod 46 which passes actually through a bore in the center of the shock system 12. The rod 46 has a sharp point which ruptures the membrane from within the pressure chamber 36 such that there is no interference with the free expansion of the gas shock wave outwardly.

The high pressure tube of the shock system can be formed to have a bore or constriction in a central portion with a wider bore at both ends. The rod 46 extends through the constricted portion but may be either hollow or fluted (not shown) such that the gas can pass by it into the lower pressure chamber region 34. At the upper end (nearest the gas source) the rod 46 is wider (of larger diameter) such that upon firing it is captured and cannot fly down through the constricted region. In this wider end region, the rod is made of a magnetically responsive metal and can be driven downwardly by the use of a solenoid 48 actuated by an electrical energizing mechanism 50. The high pressure tube that forms the shock system 12 is made of a magnetically non-responsive material such as brass as mentioned. A spring 54 between the upper enlarged end of the rod 46 and the constricted portion permits or facilitates the return of the rod to its up position at the end of each firing cycle.

When the rod 46 is actuated downwardly by the solenoid 48, its lower other end, which is sharpened, extends down into the pressure chamber 34 and pierces the membrane thereby generating a gas shock wave. At the base of the widened portion of the rod is a ring seal 56 such that, upon firing, the wider portion of the rod seals against the constriction, stopping any subsequent gas from escaping into the lower pressure chamber 34 (which has now been pressure released due to the rupture of the membrane). When the overlying gas pressure is then released, the small spring 52 returns the rod 46 to its original raised position whereby the lower pressure chamber 34 can again be closed off with a new membrane and repressurized.

Figure 6A:
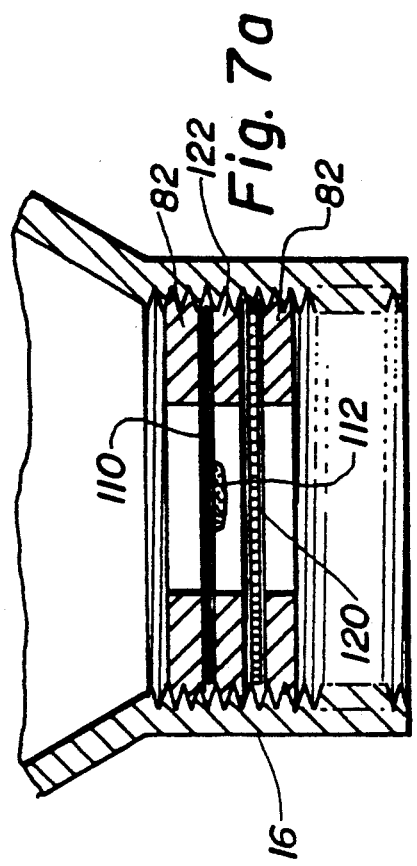
FIGS. 6a and 6b are cross sectional representations of the throat portion of the particle accelerator when constructed to operate as a fixed membrane.
Figure 6B:
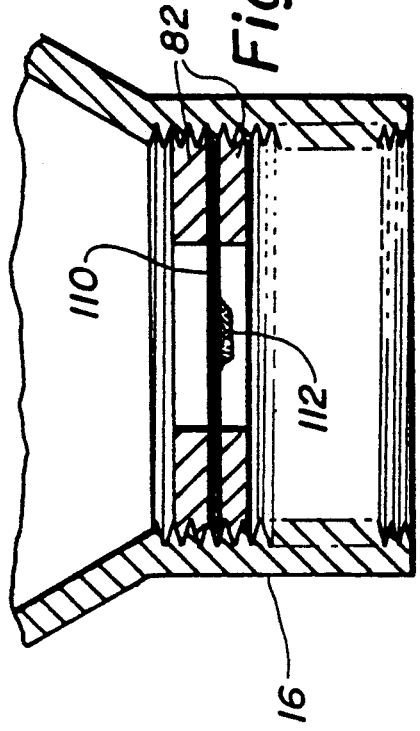

The gas shock wave which is generated with this mechanism is important because it is unlike the gas shock wave obtained by Sanford et al. with a gunpowder cartridge producing an instantaneous release of heat and shock. In the case of the gas shock system of this invention, the gas shock wave is a gas shock wave generated from a pressurized gas at ambient temperature (hereinafter referred to as a "cold" gas shock wave) which has the advantages that it does not disturb the biological material in the target region either from an ultraviolet light standpoint or from a heat standpoint both of which are undesirable when dealing with biological materials. The gas shock wave itself causes a steep increase in pressure almost amounting to a step function that is propagated through the residual gas. Generally the width of the transmission region over which the steep increase in pressure occurs is the molecular mean free path, i.e., the path distance a molecule moves before colliding with another molecule. It is the sudden catastrophic increase (referred to in the claims as "instantaneous") in pressure that is effective for providing the rapid acceleration of particles within a short distance that is necessary and desirable for this invention. The shock wave is cold. By "cold" it is meant that the gas is cool enough not to cause damage to biological materials of tissue.

The best bursts come from spontaneous membrane failures, since they fail at their tensile limit. Such membranes can be made uniformly to rupture spontaneously at a given pressure. In this case all that is needed is the gradual pressurization of the pressure chamber 34 until the critical pressure is reached which ruptures the membrane 38 and creates the gas shock wave which propagates in the direction of the target 42. The membranes may be layered. Each 2 mil Kapton ® layer breaks at pressures of 275–300 psi, with the multiple layers being additive. Metal foils may also be used.

The gas shock wave which is generated is extremely loud and potentially hazardous to an operator's hearing. Also the gas shock wave tends to become somewhat attenuated in power unless it can expand freely into a partially evacuated space. Furthermore, the particles to be accelerated by the gas shock wave, being of light weight are soon velocity attenuated if they are required to go through a gas-filled region. For these reasons a housing 14 is provided to permit the use of a partial or full vacuum in the region of the gas shock release. The housing is cylindrical and formed of two parts, an upper and a lower part 60 and 62, respectively. The two parts, 60 and 62, are joined by a snap clip 64 and a suitable O-ring 66 to provide a seal between the parts. The shock generating system 12 is threadingly engaged along the major axis 11 of the cylindrical housing 14 and is threadingly engaged at the upper end of the housing so that the system's position may be adjusted vertically within the housing 14. More specifically, the axis 11 of the chamber, as defined by the axis of the rod 46 coincide with the housing axis 11 which passes through the throat 16 and interface 18 to the target 42, all of which lie on or encompass the axis of the chamber to permit the shock wave to progress to the target.

The throat 16 forms the lower portion of the lower half 62 of the housing 14 which is tapered to form a reduced diameter throat portion 16. It is in this region that the energy of the gas shock wave is transferred to the microprojectiles for acceleration to the target. Because this energy transfer can occur by a variety of mechanisms in accordance with this invention, interchangeable inserts are placed in this region depending on the mode of use. The inserts can be threaded and screwed or otherwise fixed in place individually or can be dropped into place in the throat region as preassembled unit as will be described. A typical insert used includes some type of particle carrier 80 held by two ring inserts 82 which are threadingly engaged within the throat 16. The particle carrier 80 may be either a screen, a membrane or a combination thereof as will be described in connection with FIGS. 5 through 9, inclusive. As will be described, a nozzle/interface 18 (FIG. 1) or 18' (FIG. 2) may threadedly engage the end of the throat region. The lower end of the interface 18' is flanged inwardly and threaded to receive various attachments as is depicted in FIGS. 10 and 11.

With reference to FIG. 4, there is depicted an alternative throat section which includes a removeable insert 100 that is adapted to slide within the throat section 16' and be supported by the inwardly extending flange 102. The interior of the insert 100 is threaded to accommodate a pair of rings 82'. A small handle 84 may be provided at the upper end of the insert for convenience of handling. The lower face of the insert 100 is provided with a O-ring 104 to aid in providing a seal to prevent air leakage around the insert 100. The exterior of the insert 100 and the interior of the throat section 16 are unthreaded to facilitate the slideability of the insert. This removeable insert 100 may be used to facilitate handling of any of the alternative particle acceleration arrangements for the throat section depicted in FIGS. 5 through 9, inclusive.

The particle acceleration embodiment illustrated in FIG. *6a* and *6b* is a fixed membrane arrangement for the throat section 16 and includes a strong but resilient material such as Kapton ® polyimide films or Mylar ® polyester films. The polyimide films are exceptionally strong and thermally resistant. Polyester films have similar properties and maintain its tensile strength over a wide temperature range. Such films have sufficient strength to survive the impact of the gas shock wave. The term "resilient" is used to describe material that is capable of withstanding the shock wave without rupture up to the limit of use required. The membrane 110 is held in place about its periphery by such mechanism as rings 82 which may have a matching groove and ridge (not shown) to facilitate locking the membrane 110 in place. Locking can be accomplished by positioning the rings in the throat region 16 and tightening them down against each other with the membrane 110 between them.

Microprojectiles are adhered to the outer surface of the membrane 110 (lower surface in the drawing which is the surface closest to the target). Thus, when the gas shock wave impacts the membrane 110, it is distended but does not rupture thereby launching the microprojectiles 112 at high speed towards the target 42 (FIG. 1). This embodiment is particularly suited where it is desired to prevent damage from the driving gas impact upon the target. The membrane forms a good seal above the target and isolates it from the shock wave source. The effect of the gas shock wave on the membrane and the subsequent propulsion of the microparticles is depicted in FIG. *6b* wherein the particles 112 are seen flying to the target.

With reference to FIGS. *7a* and *7b*, another insert embodiment known as the "captured membrane" configuration as contracted to the "fixed membrane" of FIGS. *6a* and *6b* is depicted. In this case, which is very similar to that illustrated in connection with FIG. 6, a thin spacer ring 122 and a rigid screen 120 preferably made of stainless steel or similar chemically inert, nonreactive, non-toxic material 120 is captured along with the anchored membrane 110 between the rings 82. Upon firing, i.e., creation of the gas shock wave, the fixed membrane 110 distends to nearly its fullest extent, at which point (as controlled by the thickness of the spacer ring 122), it impacts against the rigid screen 120. This sudden stop results in a better release from the surface of the membrane, higher velocities for the microprojectiles and better dispersion and deagglomeration of the microprojectiles 112 than occurs in the fixed membrane embodiment of FIG. 6. This mechanism is effective even if the membrane ruptures, and captures the membrane and any membrane debris, deflecting most of the gas shock away from the target thereby providing a safe, relatively gentle mode of bombardment. A smaller disk or membrane may be attached to the back of the membrane 110, thereby reinforcing the center of the membrane and reducing its chance of rupture or if ruptures occurs ensuring that it occurs at the perimeter of the smaller membrane reducing any possible direct gas blowthrough onto the target.

Figure 11:
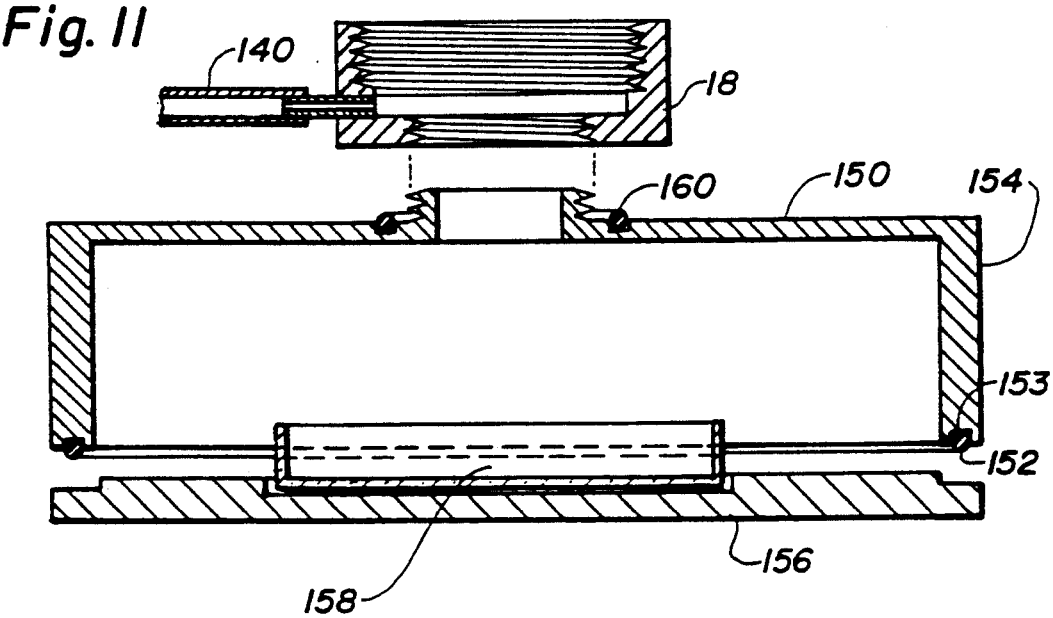
FIG. 11 is a cross sectional representation of an alternative embodiment for the nozzle portion of the particle accelerator of FIG. 1.

The embodiment depicted in FIGS. 8a, 8b and 8c, known as the "ruptured membrane" embodiment, utilizes a membrane 110 that is thinner polyimide or polyester films, or is made of weaker material than those heretofore described, (e.g., aluminum foil), such that it ruptures upon impact of the gas shock. At the moment of rupture there is a tremendous lateral shear force across the surface of the membrane, releasing the particles from the surface and deagglomerating them with very high efficiency and dispersing the particles over a relatively wide area. The initial launch of the particles is then enhanced by the flow of the gas shock wave through the region giving the particles still higher velocity. Much of the gas shock wave, however, is still reflected back into the evacuated enclosure (prior to rupture), thereby protecting the target from the worst of the gas shock. This configuration is desirable when a relatively severe shock is tolerable, where higher velocities are needed, and where excellent deagglomeration and dispersion of the microprojectiles over a wide area is needed. If the ruptured membrane generates any flying debris, a capture screen can be placed between the membrane 110 and the target 42.

An alternative embodiment of the invention depicted in FIGS. 9a, 9b and 9c, and known as the "flying disk", is depicted. In this instance, the usual membrane 110, with particles 112, that is not rupturable of the type used in the embodiment of FIG. 7, is positioned between two rings 82 and adjusted in height as desired by positioning the rings. In accordance with this invention, a relatively rigid membrane or disk 130 such as a 2 mil thick polyimide disk is positioned on the lower ring 82 but is not anchored with an overlying ring. It is simply held in place by a lip having a recess, or with a small amount of a suitable adhesive (i.e., a thin film of vacuum grease is sufficient to hold it in place). Other thickeners may be used as desired. A centering ring 132 positions a screen 134 along the axis 11 (FIG. 2) and both are supported by a lower ring 133 threaded in the throat 16. Upon firing, the disk 110 together with the particles 112 positioned on the lower side lifts off its platform and flies down the throat unimpeded until it impacts against a rigid screen 134 which is fixed in place at the bottom of the throat region by a ring support 132. Upon impact, particles are launched as in the case of the captured membrane of FIG. 7.

Potential velocities are higher than with the captured membrane of FIG. 7, although potential for the gas shock wave impacting against the target exists because gas can leak ahead of the disk while it's in flight. By using a flying disk fitted closely to the inside diameter of the region and a relatively short flight distance, the gas blowby can be small. By letting the disk, 130, upon impact, after the flight, seat in and seal against the support surface of the open screened area 134 significantly smaller than at the flying disk, the energy of the gas shock wave transmitted to the target region is kept minimal. Therefore relatively high velocities can be generated with reduced gas shock on the target area.

In another embodiment known as "gas entrainment", as seen in FIGS. 5a and 5b, a screen 134 of suitable mesh and type is used, such as a suitable screen for this purpose is Swiss Polyester Monofilament screening having 150 μm openings. Such screen is available as part no. 7-150/43 from Tetko, Inc., in Elmsford, N.Y. The screen 134 is captured between the rings 82 within the throat region 16. Microprojectiles are accelerated by the gas shock wave directly by placing them directly in the path of the gas shock wave. A drop of liquid containing the microprojectiles can be placed in the middle of the screen or mesh 134. Upon firing, the gas shock wave launches and atomizes the droplet and entrains the microprojectiles in it. The particles 112 and gas shock wave then directly impact the target 42 together. This configuration is effective when the target can tolerate the full impact of the gas shock wave.

5) Interchangeable interface for different biological targets—When the apparatus is used for intact animals, humans or other large organisms, an interface 18 is required which allows precise positioning, FIG. 10, control of flight distance to target surface, control of gas or vacuum over the target area, support of soft tissues against vacuum or shock, and the potential for dissipation of any gas shock wave which may be transmitted into this region. When smaller organisms, tissue, or cells are bombarded, a convenient mechanism for placing petri dishes or other cell containers at the proper distance within a chamber which can hold a vacuum is required. The following interface embodiments can be used.

The embodiments depicted in FIG. 10 are threefold all of which are adapted to fit on the throat portion 16. All have a tubular shaped nozzle 144 which is adapted to threadingly engage the nozzle interface 18 (FIG. 2) or 18' (FIG. 4). One version (lower right in the drawing) of the nozzle is provided with a vent tube 146. Both versions (lower left and right) have a snap-in screen 148 (similar to screen 120 (FIG. 7)) that engages a tapered recess 147 in the lower end of the nozzle. The interface 18 may be provided with a connection 140 to the vacuum pump 72 and alternatively may be provided with a connection 142 to the pressurized gas to alter the gas type within the system. An O-ring 145 is provided in a groove 149 in the upper face of the nozzles 144 to provide a seal against the lower face of the throat 18. The extended nozzle configuration is especially suited to surgical applications, where the interface is needed to be placed within a surgical opening. It also facilitates precise targeting of an area on a large surface (such as epidermis) to be bombarded. The tip of the nozzle can be pressed directly against the targeted area. At the end of the nozzle, a screen or mesh 148 can be positioned as described to support the tissue against shock and prevent the tissue from being sucked upward into the nozzle when vacuum is applied within the nozzle's interior. Any one of the differently configured nozzles can be screwed into place depending on the nature of the application.

In another embodiment, as seen in FIG. 11, a clear chamber, made of Lexan ® polycarbonate or similar shatter-resistant material, 150 can be attached to the end of the throat 18 of the gun via a threaded fitting. This embodiment, which can maintain a vacuum, has an O-ring 152 fitted in a groove 153 to maintain a seal between a side wall 154 and base plate 156. The chamber which is formed of two parts, upper half 154 which may be threadingly engaged and sealed by O-ring 160 against the interface 18 and a lower plate 156 which may be friction fitted and snapped into place and sealed by the O-ring seal 152. In this manner the chamber can readily be opened for insertion of a petri plate 158 or any small sample. This simple chamber can be used in a bench-top laboratory mode.

Figure 12:
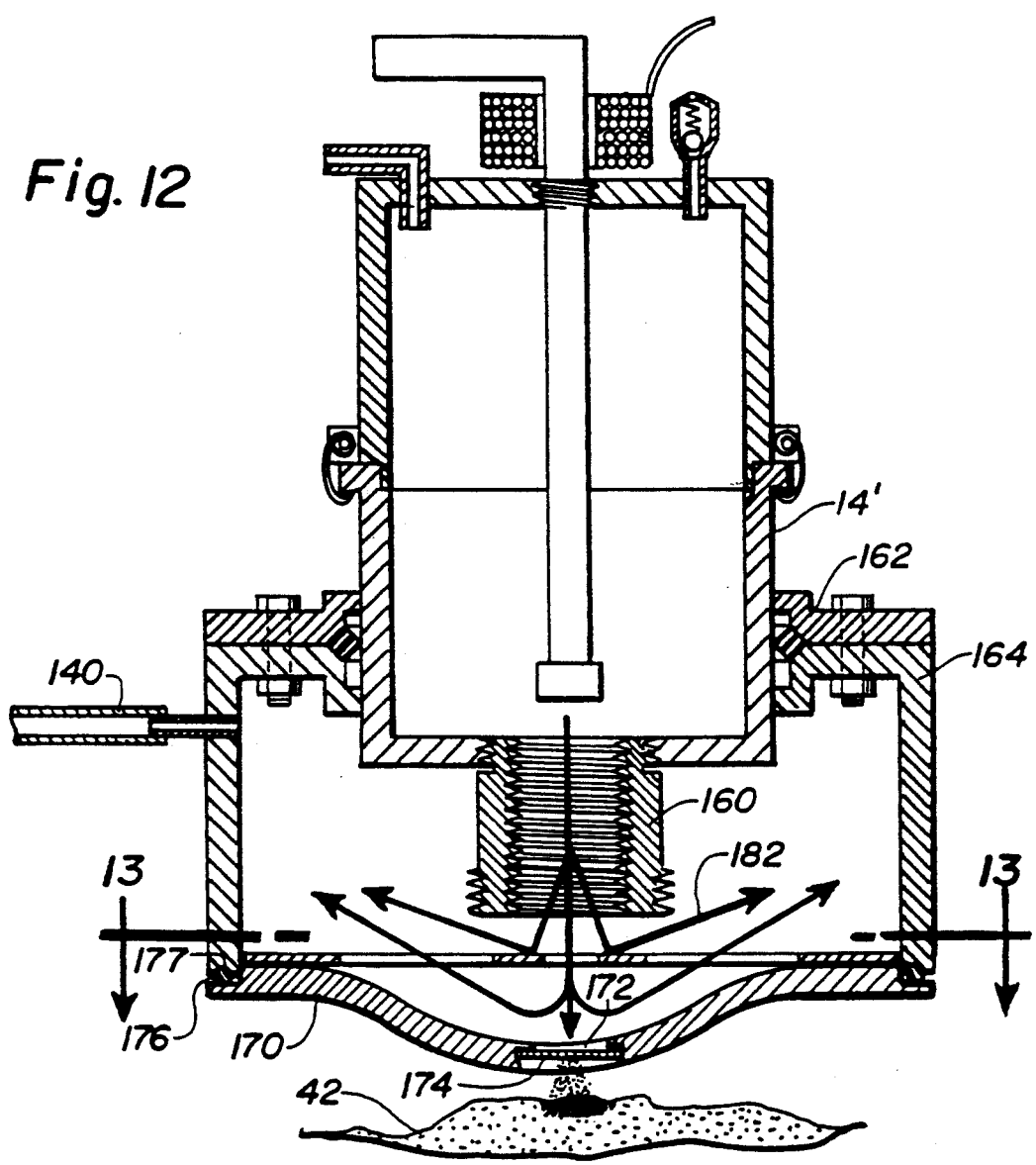
FIG. 12 is a cross sectional representation of a particle accelerator constructed in accordance with an alternative embodiment of this invention that is particularly adopted for use with large targets.
Figure 13:
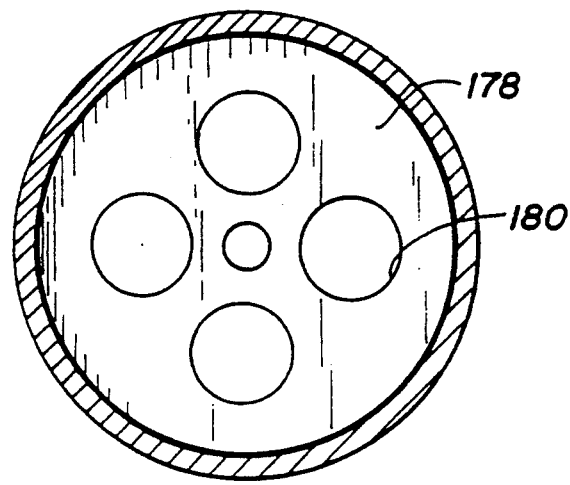
FIG. 13 is a cross sectional view of a baffle used in the accelerator of FIG. 12 taken along the section line 13—13.
Figure 14A:
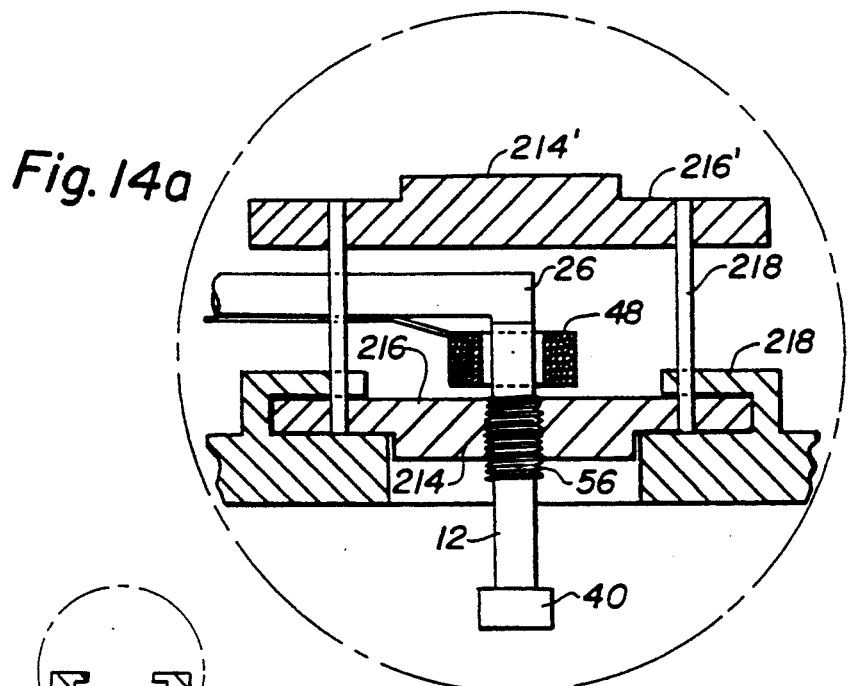
FIG. 14 is a cross sectional view of an alternative embodiment of the invention and FIG. 14a is a blown-up cross sectional representation of a portion of FIG. 14
Figure 14:
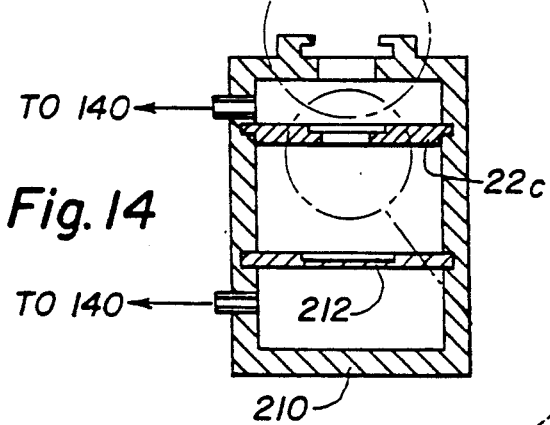
Figure 14B:
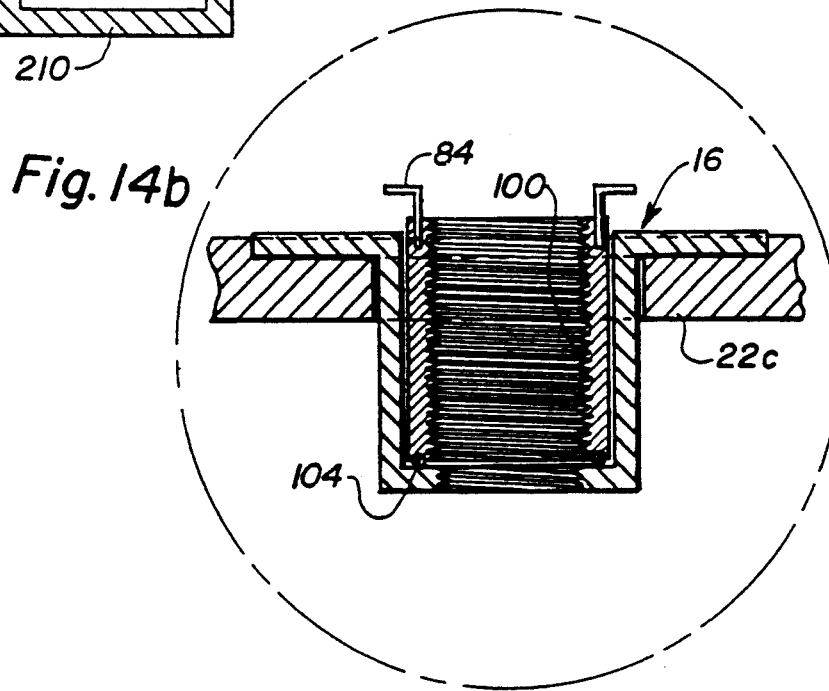
FIG. 14b is a blown-up cross sectional representation of Element 22c of FIG. 14.

As may be seen in FIG. 12 an alternative embodiment of the interface is provided which is particularly adapted to work with large animals or large surfaces. This embodiment allows maximum venting and deflection of gas blast from the target (42), while allowing minimum distance from particle launch position to target impact point. In this embodiment, the arrangement is substantially identical to that shown in FIGS. 1 and 2, the only difference being that the lower half of the housing 14 does not have to be tapered and has a threaded nozzle insert 160 of constant diameter. It may, however, be used with the chamber 14' if desired. An ante-chamber 164, in the form of an inverted housing, and cover 170 is adapted to fit on the outer portion of the housing 14' and is sealed about the periphery of the housing 14' by a grommet 162 captured between two inwardly flanged pieces of the ante-chamber 164. The lower or cover portion 170 of the ante-chamber 164 is formed to be a protuberant and relatively rigid which may as the ante-chamber be formed of Lexan®, polycarbonate or similar shatter-resistant material, as was the case for FIG. 11. The protuberant member 170 forms a orifice 172 in the center portion lying along the axis 11 of the housing 14' and is configured to accommodate a snap-in screen 174 to prevent the target tissue from being sucked up into the ante-chamber. The protuberant member 170 may be secured to the ante-chamber 164 by suitable screws (not shown). An O-ring 176 positioned a groove 177 to provide a seal maintains a vacuum.

A baffle plate 178 (FIG. 13) is placed on the protuberant member 170 and has sufficient openings 180 and closed regions to deflect most of the gas shock waves, depicted by the arrows 182, away from the target 42. FIG. 13 is a sectional view taken along the section line 13—13 of FIG. 12. The grommet 162 permits the ante-chamber 164 to be slid along the axis of the housing and thereby one is able to adjust the distance of the target 42 from the gas shock wave. The baffle 178 facilitates the flow and venting of gases laterally away from the lower orifice region to prevent the receding gases from becoming trapped in the orifice region which could result in reflection of the gases back toward the oncoming particles or simple deacceleration of the particles due to the viscous drag. The baffle plate acts finally to divert gases and the shock wave away from the lower target region.

OPERATION

In operation, the target 42 whether it be cells or tissue is selected and prepared. No special preparation is required other than possible cell plating, removal of hair, surgical exposure to tissue, etc. The particular procedures for this do not form part of this invention. Based upon the target and the objective, the optimal microprojectile type, amount, and size is chosen and prepared and loaded into place and the desired throat assembly configuration is selected and properly positioned. Finally the desired gas pressure is set at 22. The interface assembly 18 best suited to the target and purpose has been selected and the high pressure membrane is sealed in place and the housing is closed and sealed. The high pressure chamber 12 is then pressurized, the target positioned in place relative to the interface assembly and the gas environmental or degree of vacuum in the enclosure in flight areas is set. The solenoid is activated causing the unit to generate the gas shock. The vacuum is then released and the pressure to the high pressure component is vented and the process repeated as needed.

The particular manner of preparation of the biological particles, such as DNA coated particles or DNA in solution, are best loaded as a slurry in either water or ethanol used for gas entrainment, while for other configurations DNA coated particles are best loaded and spread onto the distal side of the membrane surface, suspended in ethanol and allowed to dry prior to bombardment. The particular manner of preparation of the DNA coated particles does not form part of this invention. As used herein, the term particle includes both the biological material itself, or coated on particles. Any of the well-known prior art techniques used today may be used. For example, those described in either the Agracetus patent application, or as described in Sanford et al. or Klein et al. may be used.

An alternative embodiment of the invention is illustrated in FIG. 3. In this figure, many of the essential parts of the gun described in connection with FIGS. 1 and 2 are illustrated and bear the double prime reference symbol for parts which correspond to a part in FIGS. 1 and 2. The primary difference between the embodiment of FIG. 3 is that it is reduced in size and has a pistol grip 206 to facilitate its being held for surgical applications. The hand-held pistol grip 206 is provided with switches 204 which control the several valves 28 double prime 30" along with the solenoid actuation 48 prime.

The nozzle portion 18", the throat portion 16", is similar to the throat portion 16 of FIGS. 1 and 2 and is internally threaded so that it may receive the various discs, screens, and the like as is depicted in FIGS. 5 through 9. No further infittings are provided for the apparatus illustrated so that it may be used directly on animal tissue. Although not shown, a restraining screen of the type denoted by item 148 and FIG. 10 may be used. This device also includes a valve 200 for controlling the vacuum and a line 202 for supplying power to the unit is the adapter to receive high pressure from the gas source 20 and from the vacuum pump 72. Aside from this the operation is the same as that described in connection with FIGS. 1 and 2 and need not be described further.

The cold gas shock wave generator of this invention may be retrofitted into an existing hot gas shock wave generator used in the PDS-1000 currently sold by E. I. du Pont de Nemours and Company, Wilmington, Del. The PDS-1000 is a cylindrical two chamber device shown in cross section in FIG. 14 as housing 210. Connections are made in the upper and lower sections of the device to a source of vacuum 140. The target is positioned on a platform 220 that may be slid into the device upon opening a front door to permit access to the chambers. At the top of the device is a central opening through which the cartridge used to generate the hot gas shock wave is directed. The cartridge device of the existing unit is removed and replaced with the gas shock wave generator 12 (FIG. 2). The threads 56 on the shock wave generator are threaded to engage flat disk like plates 214 and 216 which lock into place by the brackets 18 where the current barrel assembly of the PDS-1000 currently locks into place. Because this assembly will be connected with a high pressure gas source, it will be restricted in how it can be manipulated. Accordingly, the plate may have multiple notches (not shown) around its parameter so that they can be locked into place at numerous points of rotation as is most convenient. A second set of plates 214' and 216 is secured by screws 218 to the lower plates 214 and 216. However, the plates 214' and 216' are inverted in this manner. The gas shock wave generator may be removed and inverted when it is desired to replace the membrane 38 (FIG. 2) for the shock wave. This greatly facilitates changing the high pressure membranes 38. All other aspects of the high pressure gas shock wave generator remain essentially the same as previously described in connection with FIGS. 1 and 2. The chamber 210 has an upper plate 220 which also is slideable in by opening the front door to the chamber 210. This plate 220 which normally would hold the stopping plate assembly in the PDS-1000 is replaced in accordance with this invention by a throat section assembly 16 which will typically include elements 82 and 80 (FIG. 2.). More preferably, the throat assembly 16 will include the removable insert 100 illustrated in FIG. 4.. Thus, this simply can be dropped into the platform where the stopping plate assembly formerly was and the platform will retain its function as the partition is sealed between the upper and lower sections of the bombardment chamber 210. The lower section of the chamber serves as a target chamber as before, the target being depicted by the tray 212. Beyond this, the operation of the device is substantially the same as described previously.

The method and apparatus thus described may be used for enabling the transformation (or delivery of pharmaceuticals) of a variety of different living cells and tissues ranging from plants, microbes, and animals. The configurations described are suitable for use either as a handheld probe for surgical uses and large organism applications or as a non-mobile (bench mounted) device for in vitro cultures and other lab applications. A cold shock power source is used to derive the force for accelerating the particles carrying living organisms. The shock power source is enclosed within a housing which is able to hold the vacuum. The vacuum in turn facilitates the device's use and facilitates maximal rates of expansion for the gas shock wave that is generated while at the same time protecting the operator's ears from severe noise generated by the gas shock. Finally the target itself is protected from potentially lethal shocks.

The device is capable of generating a catastrophic, essentially instantaneous gas shock, without extreme heating, through the rupture of a membrane, or by similar means, thereby venting a high pressure chamber of given volume and with adjustable pressure, such that the shock wave strength and speed is suitable for accelerating microprojectiles to speeds suitable for biolistic purposes of any particular nature. Such apparatus includes housing which simultaneously protects users from the gas shock, attenuates the impact of the gas shock on the target cell or tissue, and allows use of modified internal gas environments for better particle flight characteristics. Such housing also allows optionally for relatively small, hand-held "pistol" or "wand" configurations which allow a nozzle or antechamber to be pressed directly against epidermis, dermis, or surgically exposed tissues, for biolistic treatment of large intact organisms.

The throat area of the device accommodates a variety of interchangeable assemblies which allows the device to operate in different acceleration modes ranging from a fixed membrane to a captured membrane, ruptured membrane, flying disk and gas entrainment.

A target interface area through which the accelerated particles fly on their way to the target provides interchangeable interfaces to accommodate different uses ranging from large animals to small in vitro applications. This interface area provides flexibility in what gas or vacuum the particles pass through, the distance of flight to the target, the dissipation of gas and shock prior to impact with the target and physical stabilization of the target.

In short, the apparatus and method provides a flexible transformation device that is relatively safe and provides a high degree versatility and repeatable results. The device is mobile and affords less target damage if the proper inserts are utilized. It also provides better particle distribution and dispersal along with breaking up of the agglomerated particles.

EXAMPLES

Example 1

A prototype apparatus using a cold gas shock wave for introducing particles carrying biological materials into a target of cells and/or tissue constructed in accordance with this invention (FIGS. 1 and 2) was used to transform yeast cells. The resulting number of transformed colonies and the pattern of dispersion of the transformed colonies was compared to that achieved using the PDS-1000. This apparatus is now commercialized as the PDS-1000 by E. I. du Pont de Nemours and Company, Wilmington, Del. The gunpowder driven apparatus uses a hot gas shock wave to drive a macroprojectile conveying microprojectiles coated with biological material. The macroprojectile strikes a stopping plate housing a central orifice, which stop the macroprojectile before it strikes the target and allows the microprojectile to pass through the orifice striking the target.

A growth medium (liquid YEP medium) was prepared by adding 5 g yeast extract, 10 g peptone, and 0.025 g adenine to 900 mL of distilled water, separately adding 20 g of glucose to 100 mL distilled water, autoclaving both solutions, and then combining the two autoclaved solutions. A colony of yeast cells was taken from a stock culture and placed in a 250 mL flask containing 50 mL of liquid YEP medium. The yeast cells were grown to stationary phase by placing the 250 mL flask containing the yeast cells and liquid YEP medium on a rotary shaker rotating at 150 RPM for 72 hours and 37° C. The cells are then pelleted by centrifugation, the supernatant discarded, and the cells re-suspended in 10 mL water. The concentration of the cells was determined by measuring the optical density of the suspension at 600 nm (1 unit equals approximately $2^{10}$ cells/mL). A growth medium (Uracil drop-out medium) was prepared by adding 3.35 g yeast nitrogen base without amino acids, 0.235 g Uracil dropout amino acid premix (prepared by grinding and mixing the D and L forms of the following: 0.4 g adenine, 0.4 g tryptophane, 0.4 g histidine, 0.4 g arginine, 0.4 g methionine, 0.6 g tyrosine, 1.2 g leucine, 0.6 g lysine, 1.0 g phenylalanine, and 4.0 g threonine; the mixture is stored at room temperature in a dark tightly sealed bottle), 7.5 g agar, and sorbitol and mannitol to a final concentration of 0.75 M each, separately adding 10 g glucose to 50 mL distilled water, autoclaving the two solutions, and then combining the two autoclaved solutions. $10^8$ cells were spread out onto a petri dish containing the Uracil dropout medium.

M-10 tungsten particles obtained from GTE, Hawes St., Towanda, Pa., were coated with the plasmid DNA YEP352, using the procedure described by S. A. Johnston, R. Butow, K. Shark, and J. C. Sanford, Mitochondrial Transformation in Yeast by Bombardment with Microprojectiles, Science 240:1538-1541 (1988). 5 μL of transforming DNA (1 g/μL transforming DNA in a buffer consisting of 10 mM Tris hydrochloride and 1 mM ethylenediaminetetracetic acid) was mixed with 25 μL of a suspension of M-10 tungsten particles (60 mg/μL water), to which was added 25 μL 2.5 M calcium chloride, and 5 μL 0.1 M spermidine. This mixture was allowed to sit for 10 minutes at room temperature. The mixture was then centrifuged and all of the the supernatant except for 10 μL was discarded. In preparation for bombardment, the pelleted microparticles were re-suspended in the remaining 10 μL of solution. For bombardment, 3 μL of the suspension was placed on the tip of a microprojectile.

Microparticles for use with the apparatus invention were prepared using the same procedure and were then further treated by re-suspending the particles in 50 μL of a 70% ethanol solution, and pelleting the washed microparticles by centrifugation. In preparation for introduction into the cells (bombardment), the pelleted coated microparticles were resuspended in 10 μL of a 100% ethanol solution and 3 μL of the suspension was placed on a membrane and spread to produce an even layer about 5 mm in diameter. The ethanol was allowed to evaporate at room temperature, leaving a dry powder.

Figure 7A:
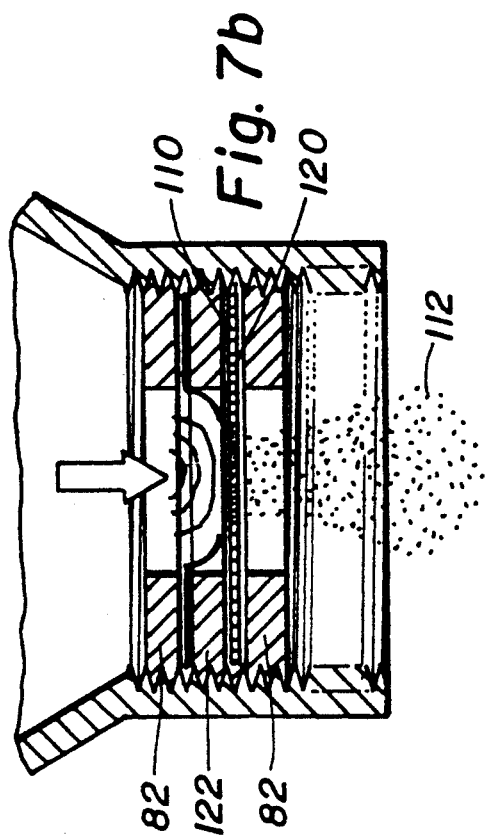
FIGS. 7a and 7b depict a cross sectional representation of the throat portion of the particle accelerator of this invention when constructed to operate as a captured membrane showing both the initial and operated conditions.
Figure 7B:
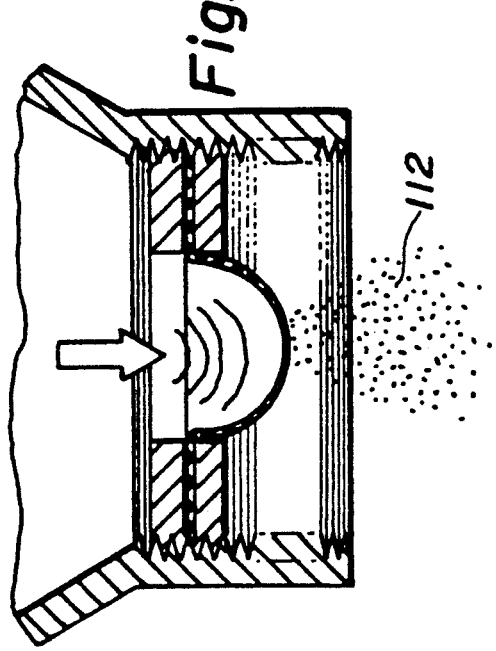
Figure 10:
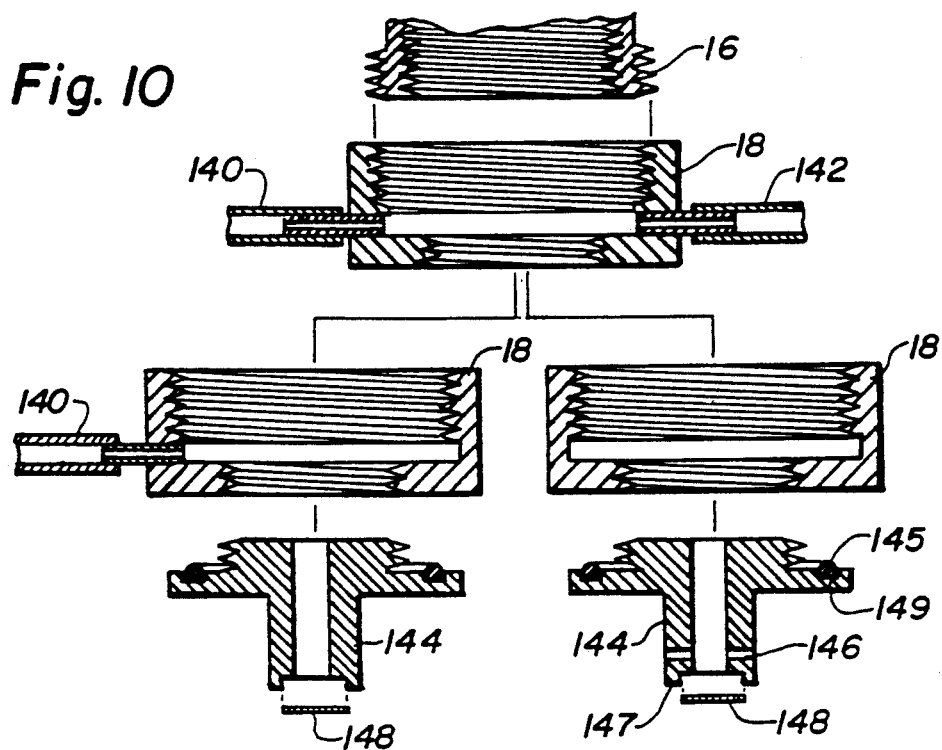
FIG. 10 depicts three alternative arrangements of the nozzle portion of the particle accelerator of FIG. 1.

Cells were bombarded with the coated microparticles the same day that they were spread onto the petri dishes containing Uracil dropout medium. Cells were bombarded with the PDS-1000. Both the top shelf and bottom shelf position were used for the target. Cells were also bombarded using the "captured membrane", "ruptured membrane", and "gas entrainment" embodiments of the present invention and the method described above in the "Operation" section and shown in FIGS. 5, 7, and 8. The desired gas (helium) pressure was selected using a high vacuum regulator at the tank source, and the presence of vacuum over the target was controlled with standard valves described. The target was placed in a Lexan ® chamber connected to a vacuum pump as disclosed in the Detailed Description of the Preferred Embodiment and shown in FIG. 10.

TABLE 1

| Colonies Method | Apparatus of the Present Invention Number of Transformed per Petri Dish | | | | |
|---|---|---|---|---|---|
| | Petri Dish No. | | | | Std. |
| | 1 | 2 | 3 | Average | Dev. |
| Helium entrainment | 149 | 352 | 1492 | 664 | 723 |
| Ruptured membrane at 500 psi | 1039 | 1623 | — | 1331 | 412 |
| Ruptured membrane at 1000 psi | 516 | 2115 | 712 | 1114 | 872 |
| Captured membrane at 600 psi | 233 | 207 | 219 | 220 | 13 |
| Captured membrane at 1000 psi | 302 | 415 | 172 | 296 | 122 |
| PDS-1000 Top shelf | 261 | 231 | 604 | 365 | 207 |
| Bottom shelf | 334 | 209 | 1215 | 586 | 548 |

Table 1 shows a comparison of the number of transformed colonies using the apparatus of the present invention and the the gunpowder driven apparatus. Results indicate that use of the "ruptured membrane" embodiment at both 500 and 1,000 psi produced approximately two to three times as many colonies as the gunpowder driven apparatus. The apparatus of the present invention also produced a wider and more even dispersion of colonies over the surface of the petri dish. The gunpowder driven apparatus typically produced a dispersion in which there was a "dead zone" of approximately 1 cm in diameter in which no transformed colonies were apparent, and in which the agar was often blown out by the blast.

Example 2

A prototype apparatus as described in Example 1 was used to transform Bacillus megaterium bacteria. The resulting number of transformed colonies and the pattern of dispersion of the transformed colonies was compared to that achieved using the PDS-1000.

50 mL of Luria-Bertani (LB) broth medium (prepared by adding 10 g tryptone, 5 g yeast extract, and 5 g NaCl, to 900 mL distilled water, adjusting the pH to 7.5 with NaOH, adding additional distilled water to a total volume of 1,000 mL, and autoclaving) was inoculated with a loop of Bacillus megaterium strain 7A17 cells, available from the Bacillus Genetic Stock Center, State University, Columbus, Ohio. The inoculated culture was incubated in a rotary shaker at 2,500 RPM for 24 hours. The culture was centrifuged and 40 mL of supernatant was discarded and the cell pellet was re-suspended in the remaining supernatant. The concentration of the cells was determined by measuring the optical density of the suspension at 600 nm. A solid growth medium (solid LB medium plus methionine and osmoticum) was prepared by adding 10 g tryptone, 5 g yeast extract, 5 g NaCl, and 15 g agar to 900 mL distilled water, adjusting the pH to pH 7.5 with NaOH, adding additional distilled water to a total volume of 1,000 mL, adding 182.2 g D-sorbitol and 136.6 g D-mannitol, autoclaving, adding a sterile solution of methionine to a final concentration of 50 μg/mL, and adding 4 mL of a sterile solution of of D,L-methionine (12.5 mg/mL). $10^8$ cells were spread out onto a petri dish containing the solid LB medium plus methionine and osmoticum. The cells were allowed to dry on the agar prior to bombardment. The medium described was optimized with respect to osmoticum concentration (sorbitol and mannitol) based on efficiency of transformation of *B. megaterium*. Increasing the concentration of osmoticum can aid in the survival of cells immediately following bombardment.

M-5 tungsten particles obtained from GTE, Hawes St., Towanda, Pa., were coated with the plasmid DNA DNA pUB110 obtained from the Becillus Genetics Stock Center in Columbus, Ohio using the procedure disclosed by Sanford et al. and as described in Example 1. The plasmid pUB110 is 4.5 kb in size and confers resistance to the antibiotics kanamycin (Km) and neomycin (Nm). The plasmid pUB110 was isolated from 24 hour old cultures of *Bacillus subtilis* strain 1EG using the method described by T. Maniatis, E. F. Firtsch, and J. Sambrook, Molecular Cloning, A Laboratory Manual, 1982. The plasmid pUB110 was then purified using a cesium chloride-ethidium bromide gradient.

Microparticles for use with the apparatus of the present invention were also prepared using the method described by Sanford et al.

Cells were bombarded with the PDS-1000 described by Sanford et al. The "captured membrane", "ruptured membrane", "flying disc", and "gas entrainment" embodiments of the present invention were tested using the procedure described above in the "Operation" section and shown in FIGS. 5, 7, and 8.

Stationary cells were plated on the medium described above (solid LB medium plus methionine and osmoticum) and were bombarded with either the gunpowderpowder driven apparatus of Sanford et al. or the apparatus of the present invention and then covered with 15 mL of an overlay medium (prepared by adding 4 mL D,L-methionine and 2 mL kanamycin sulfate (25 mg/mL solution) to 1 liter of autoclaved LB broth medium to a final concentration of 50 g/mL each). After the overlay medium hardened the petri dishes were maintained at 37° C. and the number of transformants were counted after 72 hours. Transformed *B. megaterium* cells were resistant to the antibiotics kanamycin and neomycin. Transformants were thus selected by their ability to grow in the presence of kanamycin.

Ten transformants were isolated and streaked on solid LB medium with methionine and kanamycin (10 g/mL). This kanamycin concentration is approximately the same as the concentration of kanamycin in the petri dishes containing bombardment medium and overlay medium from which the transformants were isolated. Plasmid DNA was isolated from 10 transformants. The purified plasmid DNA was cut within the restriction enzyme BamH1 and then visualized by agarose gel electrophoresis. pUB110 is cut at one site with BamH1. The digested plasmid DNA from each transformant was compared to the known markers which were lambda-phage digested with HindIII and lambda-phage digested with HindII and ECoR1 and also compared to pUB110 plasmid isolated from *B. subtilis* 1E6digested with BamH1. The digested plasmid DNA from the transformants was identical in size (4.5 kb) to plasmid pUB110 digested with BamH1. Thus the presence of transformation was confirmed in those cells selected as transformants.

The results of bombardment of *B. megaterium* with the gunpowder driven PDS-1000 apparatus and the apparatus of the present invention are shown in Table 2. Tables 3 and 4 indicate the results of bombardment experiments using various embodiments of the present invention.

TABLE 2

Comparison of Number of Transformants - Apparatus of the Present Invention Compared to the PDS-1000

| Colonies Method | Number of Transformed per Petri Dish | | | | |
|---|---|---|---|---|---|
| | Petri Dish No. | | | | Std. |
| | 1 | 2 | 3 | Average | Dev. |
| Helium entrainment at 1000 psi | 0 | 0 | 0 | 0 | 0 |
| Ruptured membrane at 600 psi | 14 | 77 | 93 | 61.3 | 41.8 |
| Ruptured membrane at 1000 psi | 8 | 0 | 7 | 5.0 | 4.3 |
| Captured membrane at 600 psi | 37 | 4 | 15 | 18.7 | 16.8 |
| Captured membrane at 1000 psi | 16 | 28 | 8 | 17.3 | 10.1 |
| PDS-1000 | 16 PETRI DISHES | | | NO COLONIES | |

TABLE 3

Comparison of Number of Transformed Colonies for Various Embodiments

| Colonies Method | Number of Transformed per Petri Dish | | | | |
|---|---|---|---|---|---|
| | Petri Dish No. | | | | Std. |
| | 1 | 2 | 3 | Average | Dev. |
| Flying disc at 800 psi | 4 | 6 | 7 | 5.7 | 1.5 |
| Flying disc at 1200 psi | 3 | 0 | 1 | 1.3 | 1.5 |
| Ruptured membrane at 600 psi | 3 | 1 | 0 | 1.3 | 1.5 |
| Ruptured membrane at 1000 psi | 0 | 1 | 1 | 0.7 | 0.6 |

Controls run:
1) Cells were mixed with DNA prior to being bombarded with naked particles using each of the embodiments above (18 petri dishes bombarded, no transformed colonies found).
2) Cells were mixed with DNA coated particles with no subsequent bombardment, (18 petri dishes prepared, no transformed colonies found).

TABLE 4

Comparison of Number of Transformed Colonies for Various Embodiments

| Colonies Method | Number of Transformed per Petri Dish | | | |
|---|---|---|---|---|
| | Petri Dish No. | | | |
| | 1 | 2 | 3 | Average |
| Ruptured membrane at 800 psi (3 cm) | 4 | 2 | 2 | 2.7 |
| Ruptured membrane at 600 psi (3 cm) | 1 | 0 | 1 | 0.7 |
| Ruptured membrane at 400 psi (3 cm) | 0 | 0 | 0 | 0 |
| Ruptured membrane at 800 psi (5 cm) | 1 | 0 | 0 | 0.7 |
| Ruptured membrane at 1200 psi | 1 | 0 | 0 | 0.7 |

TABLE 4-continued

Comparison of Number of Transformed
Colonies for Various Embodiments

| Colonies Method (3 cm) | Number of Transformed per Petri Dish |   |   |         |
|---|---|---|---|---|
|  | Petri Dish No. |   |   |         |
|  | 1 | 2 | 3 | Average |

Controls run:
Cells untreated, cells mixed with DNA and bombarded with naked particles, cells bombarded with naked particles and then mixed with particles and DNA, cells mixed with DNA and then hit with a helium shock (no particles), and cells hit with a helium shock and then mixed with DNA. 20 petri dishes tested, no transformed colonies found.

Table 2 indicates that several transformants were observed with various embodiments of the present invention while no transformants were observed with the PDS-1000. Tables 2, 3 and 4 show that the apparatus of the present invention can be used successfully to produce transformants, sometimes at relatively high rates (colonies per petri dish), which were not possible with the PDS-1000. Furthermore, transformation rates up to several thousand or more are possible under optimal conditions. The preferred conditions for achieving such high transformation rates include use of 15 hour old Bacillus cultures, a cell density of 108 cells/petri dish, use of a flying disc embodiment at 900 psi, and a cell growth medium which includes 1.0 M sorbitol and 0.75 M mannitol as osmotic support for the cells. Under these conditions, the present invention provides approximately a 1.000-fold increase in transformants per pem disk than the gunpowder driven apparatus of Sanford et al.

Example 3

A prototype apparatus for introducing particles carrying biological materials into a target of cells and/or tissue constructed in accordance with this invention was used to transform NT1 Nicotiana tabacum tobacco cells. The resulting number of transformed cells and the pattern of dispersion of the transformed cells was compared to that achieved using the PDS-1000.

NT1 Nicotiana tabacum cells were grown as suspension in a liquid growth medium (Daniell, et al. PNAS, 87:88-92, 1990) on a gyratory shaker. The NT1 cell line was obtained from G. An at the University of Washington (Daniell et al., PNSAS, 87:88-92-1990). The NT1 cells have lost their ability to regenerate into plants but are a useful model system because of their uniformity and rapid growth. The cells were generally found in clusters of three to four cells each. In preparation for bombardment, 1 to 5 mL of cell suspension was collected onto filter paper discs using a Buchner funnel.

M-10 tungsten particles obtained from GTE, Hawes St., Towanda, Pa., were coated with the plasmid DNA pIB1505 (obtained from Dr. Bill Crosby at the Molecular Genetics Plant Biotechnology, Institute, NRC Saskatoon, Canada), as the transforming DNA using the procedure described by T. M. Klein, M. E. Fromm, A. Weissinger, D. Tomes, S. Schaaf, M. Sleeten, and J. C. Sanford, Proc. Natl. Acad. Sci. 85:4305-4309, 1988, T. M. Klein, E. Fromm, T. Gradziel, and J. C. Sanford, Biotechnology 6:559-563, 1988, T. M. Klein, E. C. Harper, Z. Svab, J. C. Sanford, M. E. Fromm, P. Maliga, Proc. Natl. Acad. Sci. 85: 8502-8503, 1988, and by Sanford et al.

Microparticles for use with the apparatus of the present invention were prepared using the same procedure as in Example 1.

The β-glucuronidase gene (GUS) gene was used as a reporter gene and used to assay rates of transformation in the plant cells. The GUS gene was cloned from the bacterium E. coli (R. A. Jefferson et al., EMBO, 6:3901-3907, 1987). The GUS gene codes for the protein β-glucuronidase, which is not normally present in plant species. Plant cells which have been transformed with GUS will turn blue in the presence of the substrate x-gluc. The GUS assay was used to detect transient gene expression in bombarded NT1 plant cultures. The cells are stained two days after bombardment. The staining procedure consisted of adding 1 mL of x-gluc solution to the cells using the method described by McCabe et al., Biotechnology 6:923 (1988). The solution consisted of 0.5 mg/mL x-gluc dissolved in DMSO, 10 mM EDTA, 100 mM sodium phosphate, 0.5 mM potassium ferrocyanide, and 0.1% Triton X-100. The cells were incubated at 37° C. for 24 hours and the number of blue spots recorded.

Cells were bombarded with the PDS-1000 as disclosed by Sanford et al. and described by T. M. Klein, M. E. Fromm, A. Weissinger, D. Tomes, S. Schaaf, M. Sleeten, and J. C. Sanford, Proc. Natl. Acad. Sci. 85:4305-4309, 1988, T. M. Klein, E. Fromm, T. Gradziel, and J. C. Sanford, Biotechnology 6:559-563, 1988, and T. M. Klein, E. C. Harper, Z. Svab, J. C. Sanford, M. E. Fromm, P. Maliga, Proc. Natl. Acad. Sci. 85:8502-8503, 1988. The "flying disc" and "gas entrainment" embodiments of the present invention were tested using the procedure described above in the "Operation" section and shown in FIGS. 5, 7, and 8.

Table 5 shows a comparison of transformation of NT1 cells using the PDS-1000 and the apparatus of the present invention.

TABLE 5

Comparison of Number of Transformants - Apparatus
of the Present Invention Compared to the PDS-1000

| Colonies Method | Number of Transformed per Petri Dish |   |   |   |   |
|---|---|---|---|---|---|
|  | Replicate No. |   |   |   | Std. |
|  | 1 | 2 | 3 | Average | Dev. |
| Helium entrainment | 406 | 440 | 475 | 440.3 | 34.5 |
| Flying Disc | 773 | 610 | 603 | 662.0 | 96.2 |
| PDS-1000 | 124 | 118 | 122 | 121.3 | 3.0 |

Table 5 shows the apparatus of the present invention provides superior transformation rates in comparison to the hot gas shock wave apparatus provided by the PDS-1000.

The same procedures and plasmid described for transformation of NT1 tobacco cells were used to transform peach embryonic callus. The growth medium used for peach callus (DKW medium) consisted of 4.4 μM BAP, 0.05 μM IBA, 2% sucrose, pH 5.8, and agar (0.6-0.7%) or Girlite (0.25%). Peach callus was provided by Dr. Ralph Scorza of the USDA. The peach callus was taken from a five year old culture derived from immature embryos, were autotrophic, and were growth-regulator dependent, and could continue to produce somatic cells. In this case the peach callus was bombarded three consecutive times with the PDS-1000. The peach callus were bombarded only once using the apparatus of this invention. The results are shown in Table 6.

TABLE 6

Comparison of Number of Transformants - Apparatus of the Present Invention Compared to the PDS-1000

| Method | Number of Blue Spots (Transformed Cells) per Petri Dish | | |
|---|---|---|---|
| | Lowest # | Highest # | Average |
| Helium entrainment at 900 psi | 62.0 | 554.0 | 329.7 |
| Helium entrainment at 1200 psi | 75.0 | 320.0 | 208.0 |
| Flying Disc at 900 psi | 111.0 | 345.0 | 172.7 |
| Flying Disc at 1200 psi | 89.0 | 172.7 | 230.0 |
| PPS-1000 (triple bombardment) | 86.0 | 340.0 | 215.4 |

Table 6 shows that the apparatus of the present invention can achieve rates of gene delivery in a single bombardment, that are greater than can be achieved by three consecutive bombardments with the PDS-1000. Furthermore, the uniformity of dispersion and amount of area covered was observed to be qualitatively superior to that produced using PDS-1000.

Example 4

A prototype apparatus as described in FIG. 1 was used. The resulting number of transformed cells and the pattern of dispersion of the transformed cells was compared to that achieved using the PDS-1000.

M-10 tungsten particles obtained from GTE, Hawes St., Towanda, Pa., were coated with the plasmid DNA pHBluc obtained from R. S. Williams, Duke University, Durham, N.C. using the procedure of Sanford et al. Plasmid pHBluc was used for the transformation of myotubes in vitro and for ear, skin, and liver in situ and contains the firefly luciferase gene fused to a human beta-actin promoter in a puc19 based vector (ole Wet, J. R., et al., *Mol. Cell Biol.*, 7:725-727 (1987), Leavitt, J. et al., *Mol. Cell Biol.* 4:1961-69 (1984).

Microparticles for use with the apparatus of the present invention were purchased from Alfa Johnson, Mathy, Danvers, Mass.) and were also prepared using the method described by Sanford et al.

Myotubes were prepared from chick embryos. Chick embryos were removed from the egg and the breast muscle was removed by dissection and placed in a drop of the commercially available solution, Saline G. The muscle was minced and then diluted with 9 mL Saline G, 1 mL of a 10× solution of trypsin (2.5% solution in buffered saline). This mixture was rocked for 5 minutes and then agitated by pulling the mixture into and out of a pipet. The mixture was then rocked for an additional 15 minutes and the cells collected by filtration. The cells were re-suspended in 20 mL of CKI growth media (commercially prepared Dulbecco's Modified Eagles Medium consisting of 0.584 g/L L-glutamine, 1 g/L glucose, 3.7 g/L sodium bicarbonate, 15% horse serum, 5% embryo extract) and then counted (Embryo extract is prepared by removing 100 g of chick embryos are removed from the egg, decapitated, and then homogenized in 100 mL of a medium consisting of 121.12 g/L sodium chloride, 15.5 g/L potassium chloride, 12.72 g/L magnesium chloride, 7.8 g/L calcium chloride, 2 g/L dibasic sodium phosphate, and 5.19 g/L monobasic sodium phosphate; the homogenate was stirred in a cold room for one hour after addition of 10,000 units of hyluronidase. The mixture was centrifuged to remove debris; lipid was skimmed off the supernatant, which was then sterilized by filtration). The cells were then plated on 50 mm petri dishes at a density of $1 \times 10^6$ cells per mL. The myotubes were held for 5 days prior to bombardment.

Cells were bombarded with the PDS-1000 using standard protocols. This procedure was modified only in that the the liquid medium overlaying the myotubes was removed just prior to bombardment. The "captured membrane", embodiment of the present invention were tested using the procedure described above in the "Operation" section and shown in FIG. 5. The media was replaced immediately after bombardment. The cells were incubated for 24 hours at 37° C. and then assayed for luciferase activity.

In order to assay for luciferase activity, the cells were scraped off the plate in 1 mL of extraction buffer (consisting of 100 mM potassium phosphate buffer, pH 7.8, 3 mM magnesium chloride, and 1 mM DTT), and then pelleted by centrifugation. The supernatant was removed and 100 μL of extraction buffer and 50 μL of lysis buffer (consisting of 8.9 mL of 0.25 M Tris buffer, pH 7.8, 1.0 mL soybean trypsin inhibitor of 10 mg/mL concentration, 0.1 mL aprotinin) were added and the cells lysed by sonication for 6 seconds. The cell debris was pelleted by centrifugation and the supernatant assayed for luciferase activity.

The assay for luciferase activity measures the output of light (in photons) produced by the reaction catalyzed by the luciferase enzyme in the presence of its substrate luciferin. The quantity of light produced (number of photons) is proportional to the quantity of luciferase extracted from the tissue, which is determined by the number of transformed cells and the amount of luciferase produced by each transformed cell. The greater the luciferase activity the more efficient the transformation. The number of photons per shot area can be converted to the number of picograms of luciferase per shot area by developing a standard curve using purified commercially available luciferase.

Table 7 indicates the results of a comparison of the transformation efficiency of the apparatus of the present invention and the PDS-1000

TABLE 7

Peak Luciferase Expression: Comparison of PDS-1000 and the Wand One Day After Bombardment. Luciferase Is Expressed as Total Pico Grams from the Bombarded Area

| | Skin (10.6 cm diameter) | Ears | Myotubes (160 mm plate diameter) |
|---|---|---|---|
| | Biolistic PDS-1000 (picograms luciferase per area bombarded) | | |
| Mean | 300 | 1312 | 2959 |
| Std. Error of Mean | 64 | 202 | 306 |
| Sample Number | 17 | 59 | 6 |
| | Present Invention (picograms luciferase per area bombarded) | | |
| Mean | 1543 | 5563 | 34775 |
| Std. Error of Mean | 448 | 1510 | 5114 |
| Sample Number | 4 | 18 | 5 |

Table 7 shows that the apparatus of the present invention for myotubes produces on the average about 11 times higher luciferase activity, and therefore transformation rate, than the gunpowder driven apparatus.

In another test, the coating of microparticles and the preparation for bombardment with DNA for transformation of living in situ tissues using the PDS-1000. Gold microparticles were used instead of tungsten. Gold particles used were spherical, and either of 1 to 3 μ diameter or 2 to 5 μ in diameter (available from Alpha products, product no. 00766). In addition, the configuration of the apparatus was modified in that instead of a vacuum chamber, a nozzle (FIG. 10) was placed at the end of the device to direct the microparticles to a small patch of tissue. For skin and ear tissue the nozzle was connected to a vacuum pump so that the microparticles traveled through a reduced atmosphere. Liver tissue would have been damaged by a reduced atmosphere and was therefore not subjected to the reduced atmosphere.

Microparticles for use with the apparatus of the present invention were purchased from Alfa, Johnson, Mathey, Danvers, Mass. and also prepared using the method described by Sanford, et al.

To prepare the skin and ears for bombardment, the animal was anesthetized and its hair removed from the to be bombarded with a depilatory. An area about 6 mm in diameter was then bombarded and the animal was then allowed to recover from the anesthetic. In 24 hours the animal was sacrificed and the bombarded area is cut out. The tissue was macerated in a mixture of 140 μL of extraction buffer, 50 μL of lysis buffer, and 10 μL of 2% NP-40 detergent (commercially available). The cell debris was then pelleted by centrifugation, and the supernatant assayed for luciferase activity. The comparison tests set forth in Table 7 showed the apparatus of the present invention produces on the average about 4 times for ears, and 5 times for skin, higher luciferase activity, and therefore, transformation rate than the gunpowder driven apparatus.

To transform liver tissue, a mouse is anesthetized and an incision made in its abdomen one expose of the lobe of liver. A 10 mm area was then bombarded (as the skin and ears except without drawing a vacuum). The incision was then closed and the animal allowed to recover. In 24 hours the animal is sacrificed and the bombarded area removed, macerated in 200 μL extraction buffer, the cell debris was then pelleted by centrifugation and the supernatant assayed for luciferase activity.

Table 8 indicates the results obtained for livers bombarded with the apparatus of the present. It was not possible to transform liver with the gunpowder driven apparatus of Sanford et al.

TABLE 8

| Present Invention (captured disk) (picograms luciferase per area bombarded) | | | |
|---|---|---|---|
| Liver | 1 | 3 | 5 |
| Mean | 293 | 243 | 5 |
| Std. Error of Mean | 122 | 133 | 2.3 |
| Sample Number | 8 | 4 | 3 |

What is claimed is:

1. A method of introducing particles carrying biological materials into a target of cells, said method comprising the steps of:

providing a planar carrier sheet having a target side, said sheet being a resilient membrane fixedly secured at its edges against movement,
providing a target of cells,
positioning particles carrying biological materials on the target side of the planar carrier sheet, and
exposing said sheet to the force of an instantaneous cold gas shock wave so as to accelerate the particles free of the carrier sheet and to cause them to penetrate the surface of the cells and become incorporated into the interior of the cells without killing the cells, said cold gas shock wave causing distension but not rupture of the membrane, thereby protecting the target from the shock wave.

2. A method of introducing particles carrying biological materials into a target of cells, said method comprising the steps of:

providing a planar carrier sheet having a target side, said sheet being a resilient membrane fixedly secured at its edges against movement,
providing a target of cells,
positioning a restraining screen between the target of cells and the membrane,
positioning particles carrying biological materials on the target side of the planar carrier sheet, and
exposing said sheet to the force of an instantaneous cold gas shock wave so as to accelerate the particles free of the carrier sheet and to cause them to penetrate the surface of the cells and become incorporated into the interior of the cells without killing the cells, said restraining screen being positioned such that the membrane is restrained against the screen prior to full distension or rupture in response to said cold gas shock wave, allowing the particles to pass through the screen to the target.

3. A method of introducing particles carrying biological materials into a target of cells, said method comprising the steps of:

providing a planar carrier sheet having a target side, said sheet being a resilient membrane fixedly secured at its edges against movement,
providing a target of cells,
positioning particles carrying biological materials on the target side of the planar carrier sheet, and
exposing said sheet to the force of an instantaneous cold gas shock wave so as to accelerate the particles free of the carrier sheet and to cause them to penetrate the surface of the cells and become incorporated into the interior of the cells without killing the cells, said cold gas shock wave causing distension and rupture of the membrane, thereby launching, deagglomerating and dispersing the particles over a broad region of the target cells.

4. A method of introducing particles carrying biological materials into a target of cells, said method comprising the steps of:

providing a planar carrier sheet having a target side, said sheet being a non-resilient membrane fixedly secured at its edges against movement,
providing a target of cells,
positioning particles carrying biological materials on the target side of the planar carrier sheet, and
exposing said sheet to the force of an instantaneous cold gas shock wave so as to accelerate the particles free of the carrier sheet and to cause them to penetrate the surface of the cells and become incorporated into the interior of the cells without killing the cells, said cold gas shock wave causing distension and rupture of the membrane, thereby launching, deagglomerating and dispersing the particles over a broad region of the target cells.

5. The method of claim 4 wherein the sheet is aluminum foil.

6. A method of introducing particles carrying biological materials into a target of cells, said method comprising the steps of:

providing a planar carrier sheet, said sheet being a screen, providing a target of cells, positioning particles carrying biological materials on the screen, and exposing said screen to the force of an instantaneous cold gas shock wave so as to accelerate the particles to cause them to penetrate the surface of the cells and become incorporated into the interior of the cells without killing the cells, said screen being positioned so as to permit the force of the shock wave to pass through it to accelerate the particles by gas entrainment.

7. The method of claim 6 which includes the additional step of baffling the shock wave after it passes the screen, to deflect some of the force of the shock wave away from the target cells.

8. A method of introducing particles carrying biological materials into a target of cells, said method comprising the steps of:

providing a source of pressurized gas and a rupturable membrane seal in communication with the source of gas, providing a planar carrier sheet having a target side, providing a target of cells, positioning particles carrying biological materials on the target side of the planar carrier sheet, rupturing the seal to catastrophically release the gas so as to generate an instantaneous cold gas shock wave, exposing said sheet to the force of the instantaneous cold gas shock wave so as to accelerate the particles free of the carrier sheet and to cause them to penetrate the surface of the cells and become incorporated into the interior of the cells without killing the cells.

9. The method of claim 8 wherein the sheet is a resilient membrane fixedly secured at its edges against movement, and the cold gas shock wave causes distension but not rupture of the membrane, thereby protecting the target from the shock wave.

10. The method of claim 8 wherein the sheet is a resilient membrane fixedly secured at its edges against movement, and includes the step of positioning a restraining screen between the target cells and the membrane, such that the membrane is restrained against the screen prior to full distension or rupture, allowing the particles to be launched, passing through the screen to the target.

11. The method of claim 8 wherein the sheet is a resilient membrane fixedly secured at its edges against movement, and permitting the shock wave to cause distension and rupture of the membrane, thereby launching, deagglomerating and dispersing the particles over a broad region of the target cells.

12. The method of claim 8 further including positioning a barrier between the sheet and the target of cells, the sheet being positioned so as to be not tightly anchored in place, such that the sheet will be accelerated to move freely in the direction of the target cells until restrained by the barrier which permits the particles to move toward the target cells.

13. The method of claim 12 wherein the sheet is formed of polyimide or polyester film.

14. The method of claim 12 wherein the barrier is a screen in the path of movement of the sheet.

15. The method of claim 8 wherein the planar carrier sheet is a screen that permits the force of the shock wave to pass through it to accelerate the particles by gas entrainment.

16. The method of claim 15 which includes the additional step of baffling the shock wave after it passes the screen, to deflect some of the force of the shock wave away from the target cells.

17. A method of introducing particles carrying biological materials into a target of cells, said method comprising the steps of:

providing a source of pressurized gas, providing a planar carrier sheet having a target side, said sheet being a resilient membrane fixedly secured at its edges against movement, providing a target of cells, positioning particles carrying biological materials on the target side of the planar carrier sheet, rapidly releasing the source of gas so as to generate an instantaneous cold gas shock wave, exposing said sheet to the force of the instantaneous cold gas shock wave so as to accelerate the particles free of the carrier sheet and to cause them to penetrate the surface of the cells and become incorporated into the interior of the cells without killing the cells, said cold gas shock wave causing distension but not rupture of the membrane, thereby protecting the target from the shock wave.

18. A method of introducing particles carrying biological materials into a target of cells, said method comprising the steps of:

providing a source of pressurized gas, providing a planar carrier sheet having a target side, said sheet being a resilient membrane fixedly secured at its edges against movement, providing a target of cells, positioning a restraining screen between the target of cells and the membrane, positioning particles carrying biological materials on the target side of the planar carrier sheet, rapidly releasing the source of gas so as to generate an instantaneous cold gas shock wave, exposing said sheet to the force of the instantaneous cold gas shock wave so as to accelerate the particles free of the carrier sheet and to cause them to penetrate the surface of the cells and become incorporated into the interior of the cells without killing the cells, said restraining screen being positioned such that the membrane is restrained against the screen prior to full distension or rupture in response to said cold gas shock wave, allowing the particles to pass through the screen to the target.

19. A method of introducing particles carrying biological materials into a target of cells, said method comprising the steps of:

providing a source of pressurized gas, providing a planar carrier sheet having a target side, said sheet being a resilient membrane fixedly secured at its edges against movement, providing a target of cells, positioning particles carrying biological materials on the target side of the planar carrier sheet, rapidly releasing the source of gas so as to generate an instantaneous cold gas shock wave, exposing said sheet to the force of the instantaneous cold gas shock wave so as to accelerate the particles free of the carrier sheet and to cause them to penetrate the surface of the cells and become incorporated into the interior of the cells without killing the cells, said cold gas shock wave causing distension and rupture of the membrane, thereby launching, deagglomerating and dispersing the particles over a broad region of the target cells.

20. A method of introducing particles carrying biological materials into a target of cells, said method comprising the steps of:

providing a source of pressurized gas, providing a planar carrier sheet, said sheet being a screen, providing a target of cells, positioning particles carrying biological materials on the screen, and rapidly releasing the source of gas so as to generate an instantaneous cold gas shock wave, exposing said sheet to the force of the instantaneous cold gas shock wave so as to accelerate the particles to cause them to penetrate the surface of the cells and become incorporated into the interior of the cells without killing the cells, said screen being positioned so as to permit the force of the shock wave to pass through it to accelerate the particles by gas entrainment.

21. The method of claim 20 which includes the additional step of baffling the shock wave after it passes the screen, to deflect some of the force of the shock wave away from the target cells.

22. Apparatus for introducing particles carrying biological materials into a target of cells and/or tissue comprising:

a closed housing capable of sustaining a vacuum, the housing having a first port for applying a vacuum thereto, a major axis, and second and third ports lying on the axis, the third port defining a throat portion where particles are accelerated and the third port located on the target side of the housing, a high pressure chamber positioned in the second port and having a portion positioned toward the throat portion, the pressure chamber constructed so as to release gas stored therein to provide a gas shock wave directed toward the throat portion, means for positioning the particles in the throat portion for their acceleration by the force of the shock wave provided by the high pressure chamber through the third port toward the target, and an interface secured to the throat portion for coupling the throat portion to the target, the portion of the pressure chamber toward the throat portion being sealed by a rupturable membrane.

23. The apparatus of claim 22 wherein the membrane is constructed of polyimide film.

24. The apparatus of claim 22 wherein the chamber includes means to mechanically rupture the membrane.

25. The apparatus of claim 24 wherein the high pressure chamber has a restricted inlet to limit the rate of flow of gas into the chamber.

26. The apparatus of claim 24 wherein the means to mechanically rupture the membrane is electromagnetically actuated.

27. The apparatus of claim 24 wherein the positioning means includes a disposable carrier sheet having a target side positioned in the throat portion and constructed so that the particles can be positioned on the target side of the carrier sheet, whereby the particles can be propelled by the force of the shock wave to the target.

28. The apparatus of claim 27 wherein the carrier sheet is resilient and which further includes anchoring means to secure the carrier sheet in the throat portion by gripping the periphery of the carrier sheet, the anchoring means being positionable at various locations along the axis.

29. The apparatus of claim 28 wherein the positioning means further includes a screen secured by its edges between the carrier sheet and the target, thereby to restrain the movement of the carrier sheet, but allowing the carrier sheet to distend partially in response to the shock wave.

30. The apparatus of claim 27 wherein the carrier sheet is rupturable in response to the shock wave and which includes anchoring means to secure the carrier sheet in the throat portion by gripping the periphery of the carrier sheet, the anchoring means being positionable at various locations along the axis.

31. Apparatus for introducing particles carrying biological materials into a target of cells and/or tissue comprising:

a closed housing capable of sustaining a vacuum, the housing having a first port for applying a vacuum thereto, a major axis, and second and third ports lying on the axis, the third port defining a throat portion where particles are accelerated and the third port located on the target side of the housing, a high pressure chamber positioned in the second port and having a portion positioned toward the throat portion, the pressure chamber constructed so as to release gas stored therein to provide a gas shock wave directed toward the throat portion, means for positioning the particles in the throat portion for their acceleration by the force of the shock wave provided by the high pressure chamber through the third port toward the target, and an interface secured to the throat portion for coupling the throat portion to the target, the positioning means includes a disposable carrier sheet having a target side positioned in the throat portion and constructed so that the particles can be positioned on the target side of the carrier sheet, whereby the particles can be propelled by the force of the shock wave to the target, the carrier sheet being resilient and which includes anchoring means to secure the carrier sheet in the throat portion by gripping the periphery of the carrier sheet, the anchoring means being positionable at various locations along the axis.

32. Apparatus for introducing particles carrying biological materials into a target of cells and/or tissue comprising:

a closed housing capable of sustaining a vacuum, the housing having a first port for applying a vacuum thereto, a major axis, and second and third ports lying on the axis, the third port defining a throat portion where particles are accelerated and the third port located on the target side of the housing, a high pressure chamber positioned in the second port and having a portion positioned toward the throat portion, the pressure chamber constructed so as to release gas stored therein to provide a gas shock wave directed toward the throat portion, means for positioning the particles in the throat portion for their acceleration by the force of the shock wave provided by the high pressure chamber through the third port toward the target, and an interface secured to the throat portion for coupling the throat portion to the target, the positioning means includes a disposable carrier sheet having a target side positioned in the throat portion and constructed so that the particles can be positioned on the target side of the carrier sheet, whereby the particles can be propelled by the force of the shock wave to the target, the carrier sheet being resilient and which includes anchoring means to secure the carrier sheet in the throat portion by gripping the periphery of the carrier sheet, the anchoring means being positionable at various locations along the axis, the positioning means further includes a screen secured by its edges between the carrier sheet and the target, thereby to restrain the movement of the carrier sheet, but allowing the carrier sheet to distend partially in response to the shock wave.

33. Apparatus for introducing particles carrying biological materials into a target of cells and/or tissue comprising:
   a closed housing capable of sustaining a vacuum, the housing having a first port for applying a vacuum thereto, a major axis, and second and third ports lying on the axis, the third port defining a throat portion where particles are accelerated and the third port located on the target side of the housing,
   a high pressure chamber positioned in the second port and having a portion positioned toward the throat portion, the pressure chamber constructed so as to release gas stored therein to provide a gas shock wave directed toward the throat portion,
   means for positioning the particles in the throat portion for their acceleration by the force of the shock wave provided by the high pressure chamber through the third port toward the target, and an interface secured to the throat portion for coupling the throat portion to the target, the positioning means includes a disposable carrier sheet having a target side positioned in the throat portion and constructed so that the particles can be positioned on the target side of the carrier sheet, whereby the particles can be propelled by the force of the shock wave to the target, the carrier sheet being rupturable in response to the shock wave and which includes anchoring means to secure the carrier sheet in the throat portion by gripping the periphery of the carrier sheet, the anchoring means being positionable at various locations along the axis.

34. Apparatus for introducing particles carrying biological materials into a target of cells and/or tissue comprising:
   a closed housing capable of sustaining a vacuum, the housing having a first port for applying a vacuum thereto, a major axis, and second and third ports lying on the axis, the third port defining a throat portion where particles are accelerated and the third port located on the target side of the housing,
   a high pressure chamber positioned in the second port and having a portion positioned toward the throat portion, the pressure chamber constructed so as to release gas stored therein to provide a gas shock wave directed toward the throat portion,
   means for positioning the particles in the throat portion for their acceleration by the force of the shock wave provided by the high pressure chamber through the third port toward the target, and an interface secured to the throat portion for coupling the throat portion to the target, the portion of the pressure chamber toward the throat portion being sealed by a rupturable membrane, the positioning means includes a second membrane secured to the throat portion by means for gripping the periphery of the second membrane, the second membrane being rupturable by the shock wave, a resilient carrier sheet having a target side positioned between the second membrane and the target, the carrier sheet is not securely anchored to the throat portion, such that it can fly freely, the carrier sheet further constructed so that particles can be positioned on the target side thereof, and an anchored barrier positioned between the resilient carrier sheet and the target and constructed so as to stop the carrier sheet but allow particles to continue to the target.

35. Apparatus for introducing particles carrying biological materials into a target of cells and/or tissue comprising:
   a closed housing capable of sustaining a vacuum, the housing having a first port for applying a vacuum thereto, a major axis, and second and third ports lying on the axis, the third port defining a throat portion where particles are accelerated and the third port located on the target side of the housing,
   a high pressure chamber positioned in the second port and having a portion positioned toward the throat portion, the pressure chamber constructed so as to release gas stored therein to provide a gas shock wave directed toward the throat portion,
   means for positioning the particles in the throat portion for their acceleration by the force of the shock wave provided by the high pressure chamber through the third port toward the target, and an interface secured to the throat portion for coupling the throat portion to the target, the positioning means includes a disposable carrier sheet having a target side positioned in the throat portion and constructed so that the particles can be positioned on the target side of the carrier sheet, whereby the particles can be propelled by the force of the shock wave to the target, the interface further including a nozzle attached to the throat portion and constructed so as to pass the particles to a limited region of the target, and a screen positioned in the interface to prevent the target from being drawn into the interface.

* * * * *